US012648979B2

(12) United States Patent
Henderson et al.

(10) Patent No.: US 12,648,979 B2
(45) Date of Patent: Jun. 9, 2026

(54) **COMPOSITIONS COMPRISING SULFORAPHANE OR A SULFORAPHANE PRECURSOR AND *MORINGA* PLANT COMPONENTS**

(71) Applicant: Nutramax Laboratories, Inc., Lancaster, SC (US)

(72) Inventors: Robert Henderson, Lancaster, SC (US); Brian Cornblatt, Lancaster, SC (US)

(73) Assignee: Nutramax Laboratories, Inc., Lancaster, SC (US)

( * ) Notice: Subject to any disclaimer, the term of this patent is extended or adjusted under 35 U.S.C. 154(b) by 948 days.

(21) Appl. No.: 17/825,438

(22) Filed: May 26, 2022

(65) Prior Publication Data

US 2022/0387535 A1 Dec. 8, 2022

Related U.S. Application Data

(60) Provisional application No. 63/193,254, filed on May 26, 2021, provisional application No. 63/193,270, filed on May 26, 2021.

(51) Int. Cl.
A61K 36/185 (2006.01)
A61K 31/26 (2006.01)
(Continued)

(52) U.S. Cl.
CPC ............ A61K 36/185 (2013.01); A61K 31/26 (2013.01); A61K 36/06 (2013.01); A61K 36/07 (2013.01);
(Continued)

(58) Field of Classification Search
None
See application file for complete search history.

(56) References Cited

U.S. PATENT DOCUMENTS 6,383,495 B1 5/2002 Ramakrishna et al.
6,528,075 B1 3/2003 Brown et al.
(Continued)

FOREIGN PATENT DOCUMENTS

CN 113197929 A 8/2021
CN 114009777 A 2/2022
KR 101949105 B1 2/2019

OTHER PUBLICATIONS

Pereira et al., "Purification of a Chitin-Binding Protein from Moringa oleifera Seeds with Potential to Relieve Pain and Inflammation," Protein & Peptide Letters, 2011, vol. 18, No. 11, 8 pages.
(Continued)

*Primary Examiner* — Bethany P Barham
(74) *Attorney, Agent, or Firm* — Dickinson Wright PLLC

(57) ABSTRACT

A composition including a *Moringa* plant component for treating, preventing, reducing the occurrence of, decreasing the symptoms associated with, and/or reducing secondary recurrences of cancer in a subject is provided. The composition may comprise a *Moringa* plant component in an amount of 1 mg to 1750 mg, and sulforaphane or a sulforaphane derivative in an amount of 1 mg to 50 mg. Alternatively, the composition may comprise a *Moringa* plant component in an amount of 150 mg to 1500 mg sulforaphane precursor in an amount of 1 mg to 50 mg. The *Moringa* plant component can be *Moringa* leaf extract containing 10 mg of moringin per 1000 mg of the *Moringa* leaf extract. The composition may also include at least one of a mushroom extract or powder and a broccoli extract or powder.

12 Claims, 4 Drawing Sheets

HMOX1 Gene Expression in HepG2 Cells Treated with Moringa Leaf Extract (1.375 μg/ml) and Sulforaphane

(51) Int. Cl.

| | | |
|---|---|---|
| *A61K 36/06* | (2006.01) |
| *A61K 36/07* | (2006.01) |
| *A61K 36/31* | (2006.01) |
| *A61P 35/00* | (2006.01) |
| *C12N 9/24* | (2006.01) |

(52) U.S. Cl.
CPC .............. *A61K 36/31* (2013.01); *A61P 35/00* (2018.01); *C12N 9/2402* (2013.01); *C12Y 302/01147* (2013.01)

(56) References Cited

U.S. PATENT DOCUMENTS

| | | | |
|---|---|---|---|
| 6,582,733 | B1 | 6/2003 | Pruthi |
| 6,780,441 | B2 | 8/2004 | Solanki |
| 6,858,588 | B2 | 2/2005 | Khanuja et al. |
| 7,070,817 | B2 | 7/2006 | Kuppam |
| 7,166,299 | B2 | 1/2007 | Yoo |
| 7,344,738 | B2 | 3/2008 | Managoli |
| 7,402,569 | B2 | 7/2008 | Fahey |
| 8,226,989 | B2 | 7/2012 | Gokaraju et al. |
| 8,445,033 | B2 | 5/2013 | Vaidya |
| 8,541,383 | B2 | 9/2013 | Gokaraju et al. |
| 8,691,293 | B2 | 4/2014 | Gurin |
| 9,138,448 | B1 | 9/2015 | Sparman |
| 9,421,183 | B2 * | 8/2016 | Cornblatt ................. A61K 9/28 |
| 9,687,439 | B1 | 6/2017 | Pernodet et al. |
| 9,795,646 | B2 | 10/2017 | Gokaraju et al. |
| 10,010,572 | B2 | 7/2018 | Parris |
| 10,022,409 | B2 | 7/2018 | Carpenter et al. |
| 10,022,416 | B2 | 7/2018 | Sripathy et al. |
| 10,155,019 | B2 | 12/2018 | Choi et al. |
| 10,307,388 | B2 | 6/2019 | Venn-Watson |
| 10,383,891 | B2 | 8/2019 | Klein |
| 10,391,138 | B2 | 8/2019 | Shetty |
| 10,441,618 | B2 | 10/2019 | Sugiura et al. |
| 10,478,465 | B2 | 11/2019 | Shetty |
| 10,583,178 | B2 * | 3/2020 | Cornblatt ................. A61K 9/28 |
| 10,960,057 | B2 * | 3/2021 | Cornblatt ................. A61K 9/14 |
| 11,654,186 | B2 * | 5/2023 | Cornblatt ........... A61K 31/7028 424/474 |
| 12,064,471 | B2 * | 8/2024 | Cornblatt ............. A61K 31/375 |
| 2003/0229029 | A1 | 12/2003 | Laudadio et al. |
| 2004/0096417 | A1 | 5/2004 | Kleiman et al. |
| 2005/0084547 | A1 | 4/2005 | Subbiah |
| 2005/0089499 | A1 | 4/2005 | Moussou et al. |
| 2005/0158408 | A1 | 7/2005 | Yoo |
| 2006/0093691 | A1 | 5/2006 | Thurot et al. |
| 2006/0142241 | A1 | 6/2006 | Yoo |
| 2007/0172529 | A1 | 7/2007 | Palpu et al. |
| 2008/0182787 | A1 | 7/2008 | Upadhyay et al. |
| 2008/0193393 | A1 | 8/2008 | Dayan |
| 2009/0098230 | A1 | 4/2009 | Andrews |
| 2010/0112101 | A1 | 5/2010 | Gokaraju et al. |
| 2010/0174000 | A1 | 7/2010 | Sarrazin et al. |
| 2011/0208110 | A1 | 8/2011 | Martin |
| 2011/0293790 | A1 | 12/2011 | Ewing |
| 2012/0128607 | A1 | 5/2012 | Mandeau et al. |
| 2013/0108723 | A1 | 5/2013 | Martin |
| 2013/0302279 | A1 | 11/2013 | Simon et al. |
| 2014/0113031 | A1 | 4/2014 | Lee |
| 2014/0220220 | A1 | 8/2014 | Arday et al. |
| 2014/0242250 | A1 | 8/2014 | Wassell et al. |
| 2015/0037389 | A1 | 2/2015 | Ragot et al. |
| 2015/0148944 | A1 | 5/2015 | Chatterjee |
| 2015/0181917 | A1 | 7/2015 | Chang |
| 2015/0190369 | A1 | 7/2015 | Mbikay et al. |
| 2015/0342237 | A1 | 12/2015 | Daikeler et al. |
| 2016/0015813 | A1 | 1/2016 | Gokaraju et al. |
| 2016/0243176 | A1 | 8/2016 | Raskin et al. |
| 2016/0249668 | A1 | 9/2016 | Igarashi |
| 2017/0049676 | A1 | 2/2017 | Berry et al. |
| 2017/0065654 | A1 | 3/2017 | Rubin |
| 2017/0087125 | A1 | 3/2017 | Wu |
| 2017/0143781 | A1 | 5/2017 | Yarborough |

| | | | |
|---|---|---|---|
| 2017/0150734 | A1 | 6/2017 | Lorand et al. |
| 2018/0104293 | A1 | 4/2018 | Morazzoni et al. |
| 2018/0214502 | A1 * | 8/2018 | Lundin ..................... A61P 3/00 |
| 2018/0243357 | A1 | 8/2018 | Ilan |
| 2018/0289765 | A1 | 10/2018 | Shetty |
| 2018/0369134 | A1 | 12/2018 | Cavallino et al. |
| 2019/0069585 | A1 | 3/2019 | Haase |
| 2019/0111094 | A1 | 4/2019 | Shetty |
| 2019/0117555 | A1 | 4/2019 | Karaboga et al. |
| 2019/0209634 | A1 | 7/2019 | Vieira |
| 2019/0231882 | A1 | 8/2019 | Showell et al. |
| 2019/0240280 | A1 | 8/2019 | Gopi et al. |
| 2019/0343907 | A1 | 11/2019 | Brown et al. |
| 2020/0030401 | A1 | 1/2020 | Li et al. |
| 2020/0060322 | A1 | 2/2020 | Dimitrelos et al. |
| 2020/0069543 | A1 | 3/2020 | James et al. |
| 2021/0369753 | A1 | 12/2021 | Gubler et al. |

OTHER PUBLICATIONS

Mahajan et al., "Inhibitory Effect of n-butanol Fraction of *Moringa oleifera* Lam. Seeds on Ovalbumin-Induced Airway Inflammation in a Guinea Pig Model of Asthma," International Journal of Toxicology, 2009, vol. 28, No. 6, 9 pages.

Chodur et al., "Wild and domesticated Moringa oleifera differ in taste, glucosinolate composition, and antioxidant potential, but not myrosinase activity or protein content," Scientific Reports, 2018, vol. 8, 10 pages.

Elabd et al., "Investigating of Moringa Oleifera Role on Gut Microbiota Composition and Inflammation Associated with Obesity Following High Fat Diet Feeding," Macedonian Journal of Medical Sciences, 2018, vol. 6, No. 8, 6 pages.

Mahajan et al., "Protective Effect of Ethanolic Extract of Seeds of *Moringa oleifera* Lam. Against Inflammation Associated with Development of Arthritis in Rats," Journal of Immunotoxicology, 2007, vol. 4, 10 pages.

Malabed et al., "Characterization of the Glucosinolates and Isothiocyanates in Malunggay (*Moringa oleifera* L.) Extracts and Determination of Their Myrosinase Activity and Anticancer Properties," DLSU Research Congress, 2013, 6 pages.

Abel-Daim et al., "Ethanolic Extract of Moringa oleifera Leaves Influences NF-kB Signaling Pathway to Restore Kidney Tissue from Cobalt-Mediated Oxidative Injury and Inflammation in Rats," Nutrients, 2020, vol. 12, 20 pages.

Mcknight et al., "Moringa Tea Blocks Acute Lung Inflammation Induced by Swine Confinement Dust Through a Mechanism Involving TNF-α Expression, C-JUN N-Terminal Kinase Activation and Neutrophil Regulation," American Journal of Immunology, 2014, vol. 10, No. 2, 16 pages.

Waterman et al., "Stable, water extractable isothiocyanates from Moringa oleifera leaves attenuate inflammation in vitro," Phytochemistry, 2014, vol. 103, 22 pages.

Chuang et al., "Anti-fungal activity of crude extracts and essential oil of *Moringa oleifera* Lam," Bioresource Technology, 2007, vol. 98, 5 pages.

Siddhuraju et al., "Antioxidant Properties of Various Solvent Extracts of Total Phenolic Constituents from Three Different Agroclimatic Origins of Drumstick Tree (*Moringa oleifera* Lam.) Leaves," Journal of Agricultural and Food Chemistry, 2003, vol. 51, 12 pages.

Hamza, "Ameliorative effects of *Moringa oleifera* Lam seed extract on liver fibrosis in rats," Food and Chemical Toxicology, 2010, vol. 48, 11 pages.

Caceres et al., "Pharmacological properties of Moringa oleifera. 1: Preliminary screening for antimicrobial activity," Journal of Ethnopharmacology, 1991, vol. 33, 4 pages.

Verma et al., "In vitro and in vivo antioxidant properties of different fractions of Moringa oleifera leaves," Food and Chemical Toxicology, 2009, vol. 47, 6 pages.

Bukar et al., "Antimicrobial Profile of *Moringa oleifera* Lam. Extracts Against Some Food-borne Microorganisms," Bayero Journal of Pure and Applied Sciences, 2010, vol. 3, No. 1, 6 pages.

(56)        References Cited

OTHER PUBLICATIONS

International Search Report and Written Opinion mailed Aug. 25, 2022 for International Application No. PCT/US2022/031168, 19 pages.

Adebayo et al., "Antiproliferative Effect On Breast Cancer (MCF7) Of Moringa Oleifera Seed Extracts," African Journal of Traditional, Complementary, and Alternative Medicines, 2017, vol. 14, No. 2, 6 pages.

Dinkova-Kostova et al., "Chemical Structures of Inducers of Nicotinamide Quinone Oxidoreductase 1 (NQO1)," Methods in Enzymology, 2004, vol. 382, 26 pages.

Pawlik et al., "Sulforaphane inhibits growth of phenotypically different breast cancer cells," European Journal of Nutrition, 2013, vol. 52, 10 pages.

Mintel, "Natural Tropical Flavoured High Nutrient Superfood Powder," 2016, 3 pages.

Mintel, "Goodal Camellia Moisture Barrier Cream," 2018, 3 pages.

Mintel, "Toning Ampoule," 2021, 4 pages.

"Sulforaphane+ 602mg—Contains Broccoli Seed Extract with +30mg Glucoraphanin, Moringa Extract & Myrosinase—Supports Antioxidant Production, Detoxification, and Cellular Health," Amazon, product first available Jun. 14, 2020, <https://www.amazon.com/Sulforaphane-Supplement-000mcg-Antioxidant-Optimization/dp/B08B5LFVJW?ref _=ast_sto_dp>, 23 pages.

* cited by examiner

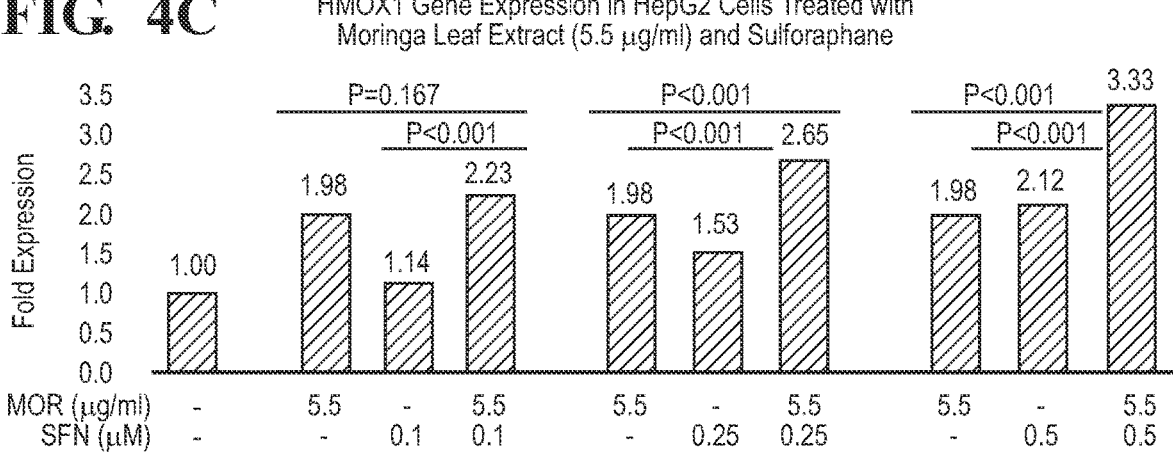
FIG. 4A HMOX1 Gene Expression in HepG2 Cells Treated with Moringa Leaf Extract (1.375 µg/ml) and Sulforaphane
FIG. 4B HMOX1 Gene Expression in HepG2 Cells Treated with Moringa Leaf Extract (2.75 µg/ml) and Sulforaphane
FIG. 4C HMOX1 Gene Expression in HepG2 Cells Treated with Moringa Leaf Extract (5.5 µg/ml) and Sulforaphane NQO1 Gene Expression in RAW264.7 Cells Treated with Moringa Leaf Extract (1.375 μg/ml) and Sulforaphane NQO1 Gene Expression in RAW264.7 Cells Treated with Moringa Leaf Extract (2.75 μg/ml) and Sulforaphane NQO1 Gene Expression in RAW264.7 Cells Treated with Moringa Leaf Extract (5.5 μg/ml) and Sulforaphane

COMPOSITIONS COMPRISING SULFORAPHANE OR A SULFORAPHANE PRECURSOR AND *MORINGA* PLANT COMPONENTS

This patent application claims priority to U.S. Provisional Application No. 63/193,254, filed May 26, 2021, and U.S. Provisional Application No. 63/193,270, filed May 26, 2021, the contents of which are incorporated herein by reference in their entirety.

TECHNICAL FIELD

The present invention generally relates to compositions comprising sulforaphane or a sulforaphane precursor and one or more *Moringa* plant components, along with methods relating to these compositions.

BACKGROUND OF THE INVENTION

The use of natural products is becoming increasingly popular with humans and non-human animals. Some of these natural products are being incorporated into dietary supplements and medical foods. There is a need in the art for supplements which are useful as chemoprotective, chemotherapeutic, anti-neoplastic and/or antioxidant agents.

Chemoprotection through the use of natural products is evolving as a safe, effective, inexpensive, easily accessible, and practical means to prevent or reduce the occurrence of many conditions affecting humans and animals. It is known that carcinogens which can damage cells at the molecular level are often ingested and inhaled as non-toxic precursors. These non-toxic precursors may then be converted into carcinogenic substances in the body. Chemoprotective agents, such as natural substances which can activate detoxifying enzymes or their co-factors, can counteract and allow for the elimination or potentiate the other naturally existing defenses such as the immune system.

Some natural products have antioxidant activity. Oxidative stress plays a major role in aging, the progression of neurodegenerative diseases as well as physiological trauma, such as ischemia. Antioxidant agents can reduce or inhibit the oxidation of vital biomolecules and may play a role in treating, preventing, or reducing the occurrence of cancer, coronary heart disease, stroke, and neurodegenerative diseases, Alzheimer's Disease, dementia, and stroke are examples of conditions affected by oxidative stress.

Cancers may result from exposure to environmental challenges—whether from within (i.e. —estrogen, progesterone hormones) or externally (i.e. —bisphenol A (BPA) from plastic)—and chronic inflammation. Fortunately, the damage from environmental challenges can be negated via a complex network of Phase II chemoprotective enzymes found in many cell types of our body. It is well known that estrogens and their metabolites can lead to the proliferation of breast tissue and tumors. Worse, the quinone estrogen metabolites have the capacity to enter the breast tissue and migrate into the nucleus of ductal and glandular epithelial cells. There, they bind to DNA forming quinone estrogen DNA adducts which lead to downstream mutations. These mutations are thought to be responsible for the very foundation of a tumor: cancer initiation. Fortunately, a particular phase II enzyme, NAD(P)H:quinone oxidoreductase (NQO1) can take dangerous and highly reactive quinone estrogens and metabolize them to inert chemicals that can readily be removed from the body. Thus, a major mechanism to decrease cancer incidence is to induce protective Phase II enzymes including NQO1. Increased levels of NQO1 can be effective at treating, preventing, repairing, reducing the occurrence of, decreasing the symptoms associated with any conditions which are resulting from high levels of quinone estrogens. Examples of quinone estrogens include, but are not limited to catechol quinones of estrogen. Quinone estrogens are described in the following references, each of which is incorporated by reference in its entirety: Nutter et al. Chem Res Toxicol, 1994, 7:23-28; Cavalieri et al. Ann N Y Acad Sci, 2006; 1089:286-301; Bolton et al. Chem Res Toxicol, 2008, 21(1):93-101; and Cavalieri et al., Biochimica et Biophysica Acta, 2006, 1766:63-78.

An example of a natural product thought to have chemoprotective and antioxidant properties is sulforaphane. Sulforaphane is an organosulfur compound which is also known as 1-isothiocyanato-4-methylsulfinylbutane. The sulforaphane precursor, glucoraphanin, can be obtained from vegetables of the Brassicaceae family, such as broccoli, brussels sprouts, and cabbage. However, copious amounts of vegetables must be consumed in order to obtain levels adequate for chemoprevention. Glucoraphanin is converted into sulforaphane by a β-thioglucosidase enzyme called myrosinase, which occurs in a variety of exogenous sources such as Brassicaceae vegetables, *Moringa* trees, and endogenously in the gut microflora. However, upon ingestion of glucoraphanin, not all animals are capable of achieving its conversion to sulforaphane, most likely due to variations in microflora populations and overall health. In addition, in acidic environments such as the stomach, glucoraphanin can be converted to inert metabolites. The active metabolite, sulforaphane, induces nuclear erythroid-2-related factor (Nrf2) which, in turn, upregulates the production of Phase II detoxification enzymes and cytoprotective enzymes such as glutathione S-transferases, NAD(P)H:quinone oxidoreductase (NQO1), and heme-oxygenase-1 (HO-1). Sulforaphane has been thought to induce the production of these enzymes without significantly changing the synthesis of P-450 cytochrome enzymes. The upregulation of Phase II enzymes is thought to play a role in a variety of biological activities, including the protection of the brain from cytotoxicity, the protection of the liver from the toxic effects of fat accumulation, and the detoxification of a variety of other tissues.

Sulforaphane and its precursor glucoraphanin have been studied extensively. Shapiro at al. (Nutrition and Cancer, (2006), Vol. 55(1), pp. 53-62) discuss a clinical Phase I study determining the safety, tolerability, and metabolism of broccoli sprout glucosinolates and isothiocyanates. Shapiro et al. discuss a placebo-controlled, double-blind, randomized clinical study of sprout extracts containing either glucosinolates such as glucoraphanin or isothiocyanates such as sulforaphane in healthy human subjects. The study found that administration of these substances did not result in systematic, clinically significant, adverse effects. Ye et al., (Clinica Chimica Acta, 200, 316:43-53) discuss the pharmacokinetics of broccoli sprout isiothiocyanates in humans.

The Moringaceae Dumort is a mono-generic genus plant family with 13 known species: *Moringa arborea, Moringa borziana, Moringa concanensis, Moringa drouhardii, Moringa hildebrandtii, Moringa longituba, Moringa oleifera, Moringa ovalifolia, Moringa peregrina, Moringa pygmaea, Moringa rivae, Moringa ruspoliana and Moringa stenopetala*. Of these 13 species, *Moringa oleifera* (synonymous with *Moringa pterygosperma*) is the most widely known and utilized species. The *Moringa* family genus of trees is also known as the horseradish trees or drumstick trees, whereas in some parts of the world it is also known as the Ben oil tree, benzolive, kelor, marango, mlonge, mulangay, nébéday, saijhan, and sajna, and under many other regional names. The leaves, seeds, fruits, fruit pods, roots, flowers, and bark of the *Moringa* trees have long been known for their nutritional and curative properties. Medicinally, various parts of *Moringa* are generally known for their multiple pharmacological effects including their antitumor, antihyperglycemic, and anti-inflammatory effects. For example, recent research has shown *Moringa* to be a potential source for antitumor activity. O-Ethyl-4-(α-L-rhamnosyloxy)benzyl carbamate together with 4(α-L-rhamnosyloxy)-benzyl isothiocyanate, niazimicin and 3-O-(6'-O-oleoyl-β-D-glucopyranosyl)-β-sitosterol, all found in *Moringa*, have been tested for their potential antitumor promoting activity using an in vitro assay which showed significant inhibitory effects on Epstein-Barr virus-early antigen. Glucomoringin is the predominant glucosinolate contained in *moringa* leaf extract. Through a hydrolysis transformation reaction, the enzyme myrosinase converts glucomoringin to the bioactive isothiocyanate 4-[(α-1-rhamnosyloxy)benzyl]isothiocyanate (moringin). Isothiocyanates are chemicals that are able to induce the production of Nrf-2-regulated Phase 2 enzymes which 1.) promote the metabolism and excretion of toxins and 2.) provide antioxidant activity. Additionally, isothiocyanates exert anti-inflammatory activity via the inhibition of the NFk-B pathway.

Niazimicin has been proposed to be a potent chemopreventive agent in chemical carcinogenesis. The *Moringa* seed extracts have also been found to be effective on hepatic carcinogen metabolizing enzymes, antioxidant parameters and skin papillomagenesis in mice. A seed ointment was found to have a similar effect to neomycin against *Staphylococcus aureus* pyodermia in mice. It has also been found that niaziminin, a thiocarbamate from the leaves of *M. oleifera*, exhibits inhibition of tumor-promoter-induced Epstein-Barr virus activation.

A number of mushrooms have been used or studied for their medicinal effects. These "medicinal mushrooms" are thought to have beneficial properties, such as antiviral, antimicrobial, anticancer, antihyperglycemic, and/or anti-inflammatory activity. Examples of medicinal mushrooms include maitake, shiitake, reishi, cremini, almond, chestnut, wood ear, cloud ear, porcini, ink cap, yarta gunbu, enokitake, shemeji, tiger milk, morel, bamboo, golden oyster, pink oyster, king oyster, hiratake, cauliflower, white jelly, golden jelly, matsutake, Mexican truffle, and straw mushrooms.

Maitake mushrooms (*Grifola frondosa*) are edible mushroom consumed widely as food and used in traditional medicine to enhance immune function and to treat cancer. Maitake mushrooms, which contain glucans, are thought to have beneficial properties, such as antitumor and immunomodulatory effects. There exist standardized extracts from maitake mushroom that contain as active ingredients glucans such as protein-bound beta-glucans. Beta 1,6-glucan, a protein bound polysaccharide, has been identified as an active constituent in maitake mushrooms. Maitake mushrooms have been demonstrated to have antitumor effects, inhibiting tumor metastasis in vitro. In one study, tumor regression or significant improvements in symptoms were observed in half of the subjects using maitake extract. In a study of postmenopausal breast cancer patients, oral administration of maitake extract was shown to have immunomodulatory effects.

Shiitake mushrooms (*Lentinula edodes*) are edible mushrooms native to East Asia. Shiitake mushrooms contain mycochemicals, which are postulated to have antiviral, antibiotic, anti-inflammatory, antihypertensive and anticarcinogenic effects. This is thought to be largely a result of glucans, both alpha and beta glucans. Some shiitake mushroom extracts have alpha glucan content greater than 40%. Additionally, lentinan (1,3 beta-D-glucan), a polysaccharide isolated from shiitake, has been well studied and is thought to play a role in shiitake's beneficial effects. It has been shown to have anticancer effects in colon cancer cells, which may be due to its ability to suppress cytochrome P450 1A enzymes that are known to metabolize pro-carcinogens to active forms. Lentin, the protein component, has strong antifungal properties and has been found to inhibit proliferation of leukemic cells and suppress the activity of human immunodeficiency virus-1 reverse transcriptase.

Reishi mushrooms (*Ganoderma lucidum*), also known as lingzki mushrooms, are edible mushrooms found in East Asia. Reishi mushrooms are thought to have anti-tumor, anti-cancer, immunomodulatory, and immunotherapeutic effects. Reishi mushrooms have a number of components which are thought to contribute to its activity, including glucan, such as beta-glucan, canthaxanthin, sterols, coumarin, ganoderic acid, and mannitol.

Baker's yeast (*Saccaromyces cerevisiae*) can be a source of glucans, in particular, beta-glucans. The active components of Baker's yeast can be extracted in a number of ways, such as the methods described in Bacon et al. Biochem J, 1969, 114(3): 557-567, U.S. Pat. Nos. 7,803,605; 5,702,719; and 8,323,644, each of which is incorporated by reference in its entirety.

Glucans are described in the following references, which are each incorporated by reference in its entirety: Vetvicka et al. Endocr Metab Immun Disord Drug Targets, 2009, 9(1):67-75, and Vetvicka et al. J Med Food, 2008: 11(4): 615-622.

Zhang et al. (Proc. Natl. Acad. Sci., (1994), Vol. 91, pp. 3147-3150) discusses a study in Sprague-Dawley rats to determine the anticarcinogenic activities of sulforaphane and structurally related synthetic norbornyl isiothiocyanates. The study determined that administration of sulforaphane was effective in blocking the formation of mammary tumors.

Cornblatt et al. (Carcinogenesis, (2007), Vol. 38(7): pp. 1485-1490) discusses a study in Sprague-Dawley rats to determine the effect of sulforaphane in chemoprevention in the breast. The study determined that oral administration of either sulforaphane resulted in a 3-fold increase in NAD(P)H:quinone oxidoreductase (NQO1) enzymatic activity and a 4-fold elevated immunostaining of the heme oxygenase-1 (HO-1) enzyme in the mammary epithelium.

Munday et al. (Cancer Res, (2008), Vol. 68(5): pp. 1593-1600) discusses a study regarding the effects of a freeze-dried aqueous extract of broccoli sprouts on bladder cancer development in rats. The study found that administration of the broccoli sprout extract resulted in a significant induction of glutathione S-transferase and NAD(P)H:quinone oxidoreductase 1 in the bladder, which are enzymes having protective activity against oxidants and carcinogens.

Fang et al. (J Altern Complem Med, (2006), Vol. 12(2): pp. 125-132) discloses a study determining the antiproliferative effect of an ethyl acetate fraction of shiitake mushrooms on human breast carcinoma cell lines (MDA-MB-453 and MCF-7), a human nonmalignant breast epithelial cell line (MCF-10F), and two myeloma cell lines (RPM108226 and IM-9). The study found that the inhibition of growth of tumor cells by the components in shiitake mushrooms may result from the induction of apoptosis.

Kim et al. (J Med Food, (2007), Vol. 10(1): pp. 25-31) discloses a study investigating the activation of natural killer (NK) cells and anticancer effects of an exo-biopolymer from rice bran cultured from *Lentinus edodes*. The study found that the exo-biopolymer may be effective for preventing and/or treating cancer through natural killer cell activation.

Louie et al. (BJUI, (2009), Vol. 153(9): pp. 1215-1221) discusses the synergistic effect of the combination of interferon-.alpha. and maitake mushroom D-fraction (PDF), a bioactive mushroom extract on anticancer activity of interferon-.alpha. in bladder cancer T24 cells in vitro.

Masuda et al. (Biol. Pharm. Bull. (2008), Vol. 31(6): pp. 1104-1108) discusses a study assessing the anti-metastatic activity of a fraction of maitake mushrooms in a murine model of lung metastasis. The study found that the fraction inhibited tumor metastasis by activation of natural killer cells and antigen-presenting cells (APCs) and suppressing adhesion molecules such as ICAM-1, leading to the inhibition of tumor cell adhesion to vascular endothelial cells.

European Patent Application No. 2 213 280 discloses formulations comprising glucosinolates such as glucoraphanin, and myrosinase, wherein the formulation is encapsulated or coated.

All references cited herein are incorporated by reference in their entirety.

SUMMARY

One aspect of the invention provides a composition comprising a *Moringa* plant component in an amount of 1 mg to 1750 mg; and sulforaphane or a sulforaphane derivative in an amount of 1 mg to 50 mg.

Another aspect of the invention provides a composition comprising a *Moringa* plant component an amount of 150 mg to 1500 mg; and a sulforaphane precursor in an amount of 1 mg to 50 mg.

Yet another aspect of the invention provides a composition comprising a *Moringa* plant component; sulforaphane, a sulforaphane derivative, or sulforaphane precursor; and at least one of a mushroom extract or powder and a broccoli extract or powder.

BRIEF DESCRIPTION OF THE DRAWINGS

The accompanying drawings incorporated in and forming a part of the specification, illustrate several aspects of the present invention, and together with the description serve to explain the principles of the invention. In the drawings:

FIGS. 4A-4C are graphs showing the results of the experiment described in Example 8.

DETAILED DESCRIPTION OF THE INVENTION

Figure 1:
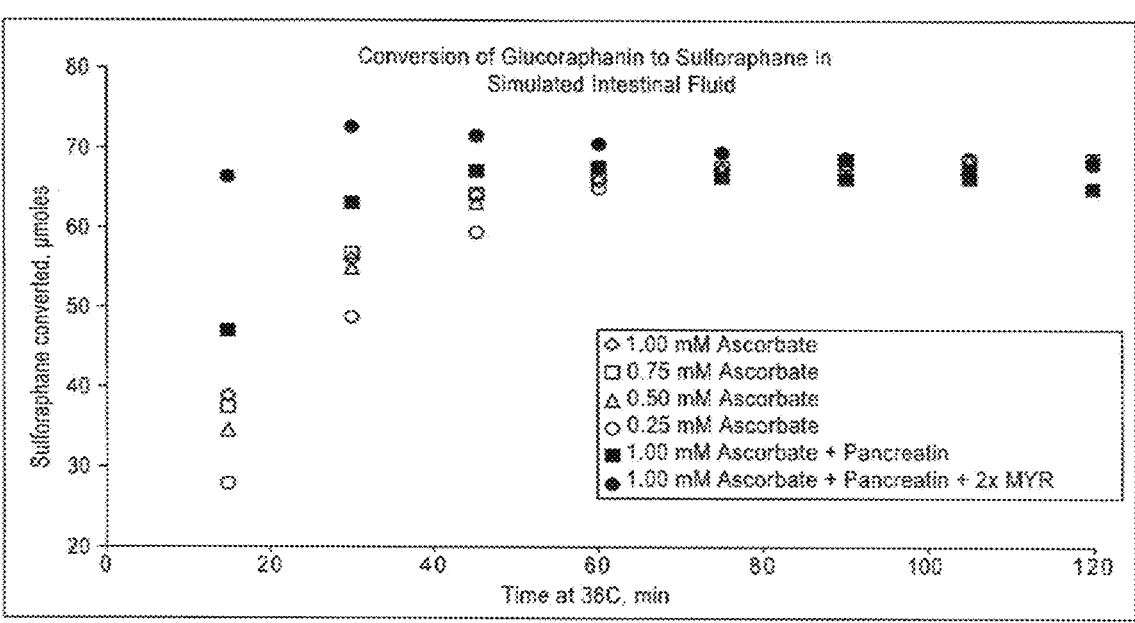
FIG. 1 is a graph showing the conversion of glucoraphanin to sulforaphane in simulated intestinal fluid, as described in Example 5.

The present invention relates to a composition including a combination of sulforaphane or a sulforaphane precursor and one or more *Moringa* plant components. In one embodiment, the *Moringa* plant component includes an enzyme capable of converting the sulforaphane precursor to sulforaphane. The composition can also include an enzyme potentiator. The combination may also include a mushroom (such as maitake, shiitake, or reishi mushroom) extract or powder. The present invention also relates to the combination of broccoli extract or powder, sulforaphane, or a derivative thereof and one or more *Moringa* plant components as a source of phytochemicals. The present invention also relates to the combination of a broccoli extract or powder, sulforaphane, or a derivative thereof and one or more *Moringa* plant components. The present invention also relates to the use of one or more *Moringa* plant components, with a mixture of one or more of the following: sulforaphane precursor, sulforaphane or a derivative thereof, and broccoli extract or powder. The present invention also relates to a composition including the combination of sulforaphane or a sulforaphane precursor, one or more *Moringa* plant components, and at least one glucan. The present invention provides compositions relating to these combinations.

The present invention also provides methods comprising forming, manufacturing, processing, and/or administering these combinations. In some embodiments, the combination may be administered for treating, preventing, reducing the occurrence of, decreasing the symptoms associated with, and/or reducing secondary recurrences of cancer, including breast cancer, prostate cancer, colon cancer, lung cancer, and bladder cancer in a subject, comprising administering to the subject.

Sulforaphane is also known as 1-isothiocyanato-4-methylsulfinylbutane. Derivatives of sulforaphane include, but are not limited to sulfoxythiocarbamate analogues of sulforaphane, 6-methylsulfinylhexyl isothiocyanate (6-HITC), and compounds which comprise the structure of sulforaphane with different side chains and/or various lengths of spacers between the isothiocyanato and sulfoxide groups. Examples of derivatives of sulforaphane include those described in the following references, each of which is incorporated herein by reference: Hu et al., Eur J Med Chem, 2013, 64:529-539; Ahn et al., Proc Natl Acad Sci USA, 2010, 107(21):9590-9595; and Morimistu et al., J. Biol. Chem. 2002, 277:3456-3463, and Baird et al., Arch Toxicol, 2011, 85(4):241-272.

In some embodiments, the composition comprises sulforaphane or a sulforaphane derivative thereof, preferably sulforaphane, in an amount of about 1 μg to about 10 g, preferably about 3 μg to about 5 g, preferably about 5 μg to about 1000 mg, preferably about 7 μg to about 750 mg, more preferably about 10 μg to about 500 mg, and most preferably about 100 μg to about 100 mg.

In some embodiments, compositions suitable for human use comprise about 1 mg to about 20 mg. For example, the compositions can include about 1 mg to about 50 mg, 15 mg to 35 mg, 1 mg to 15 mg, or 1 mg to 12 mg, of sulforaphane or sulforaphane derivative.

In some embodiments, the methods of the present invention comprise administration of sulforaphane or a derivative thereof to a subject, preferably sulforaphane, in an amount of about 1 μg to about 10 g, preferably about 3 μg to about 5 g, preferably about 5 μg to about 1000 mg, preferably about 7 μg to about 750 mg, more preferably about 10 μg to about 500 mg, and most preferably about 100 μg to about 100 mg.

In some embodiments wherein the subject is human, the method comprises administration of about 1 mg to about 20 mg. For example, the methods can include administration of sulforaphane or a derivative thereof to a subject, preferably sulforaphane, in an amount of about 1 mg to about 50 mg or 1 mg to 15 mg.

In some embodiments, the methods of the present invention comprise administration of sulforaphane or a derivative thereof to a subject, preferably sulforaphane, in an amount of about 0.01 µg/kg to about 0.2 g/kg, preferably about 0.05 µg/kg to about 0.07 g/kg, more preferably about 0.07 µg/kg to about 15 mg/kg, more preferably about 0.1 µg/kg to about 11 mg/kg, and most preferably about 0.2 µg/kg to about 7 mg/kg. In some embodiments wherein the subject is human, the method comprises administration of about 2 µg/kg to about 2 mg/kg, and more preferably about 0.01 mg/kg to about 0.3 mg/kg. The above amounts may refer to each dosage administration or a total daily dosage. The total daily dosage refers to the total amount of a compound or ingredient which is administered to a subject in a twenty-four hour period.

In some embodiments, the method comprises administration of more than one of a sulforaphane or a derivative thereof. In some embodiments, the compositions comprise more than one of a sulforaphane or a derivative thereof. For example, the methods or composition may comprise both sulforaphane and one or more derivatives thereof, or two or more derivatives. In some embodiments wherein the method or composition comprise more than one of a sulforaphane or a derivative thereof, the above amounts may refer to the amount of each sulforaphane or a derivative thereof, or the total amount of the more than one sulforaphane or derivative thereof.

The term "sulforaphane precursor" refers to any compound, substance or material which can be used to produce sulforaphane. In some embodiments, the sulforaphane precursor comprises a compound which can be converted or metabolized to sulforaphane, preferably by an enzyme. In some embodiments, the sulforaphane precursor comprises glucoraphanin. Glucoraphanin is a glucosinolate which is also known as 4-methylsulfinylbutyl glucosinolate and 1-S-[(1E)-5-(methylsulfinyl)-N-(sulfonatooxy)pentanimidoyl]-1-thio-.beta.-D-glucopyranose.

In some embodiments, the composition comprises about 1 µg to about 10 g, preferably about 250 µg to about 5 g, more preferably about 500 µg to about 2000 mg, even more preferably about 1 mg to about 750 mg, even more preferably about 1.5 mg to about 250 mg, even more preferably about 2 mg to about 100 mg, and most preferably about 3 mg to about 75 mg of the sulforaphane precursor, preferably glucoraphanin. In some embodiments, compositions suitable for human use comprise about 1 mg to about 50 mg, 1.2 mg to 12 mg, 15 mg to 35 mg, or 3.5 mg to 50 mg of the sulforaphane precursor, preferably glucoraphanin.

In some embodiments, the method comprises administering the sulforaphane precursor, preferably glucoraphanin to a subject, in an amount of about 1 µg to about 10 g, preferably about 250 µg to about 5 g, more preferably about 500 µg to about 2000 mg, even more preferably about 1 mg to about 750 mg, even more preferably about 1.5 mg to about 250 mg, even more preferably about 2 mg to about 100 mg, and most preferably about 3 mg to about 75 mg. In some embodiments wherein the subject is a human, the method comprises administration of about 1 mg to about 50 mg, 1.2 mg to 12 mg, 15 mg to 35 mg, or 3.5 mg to 50 mg of sulforaphane precursor.

In some embodiments, the method comprises administering an amount of sulforaphane precursor to a subject in an amount of about 1 µg/kg to about 1000 mg/kg, preferably about 5 µg/kg to about 500 mg/kg, more preferably about 7.5 µg/kg to about 100 mg/kg, even more preferably about 10 µg/kg to about 25 mg/kg, and most preferably about 25 µg/kg to about 10 mg/kg. In some embodiments wherein the subject is a human, the method comprises administration of about 50 µg/kg to about 800 µg/kg. The above amounts may refer to each dosage administration or a total daily dosage.

In some embodiments, the method comprises administration of more than one sulforaphane precursor. In some embodiments, the composition comprises more than one sulforaphane precursor. In some embodiments wherein the method or composition comprises more than one sulforaphane precursor, the above amounts may refer to the amount of each sulforaphane precursor, or the total amount of the sulforaphane precursors.

The sulforaphane precursor may be converted or metabolized to sulforaphane. In some embodiments, the sulforaphane precursor is converted to sulforaphane by an enzyme. In some embodiments, the enzyme capable of converting the sulforaphane precursor to sulforaphane comprises a glucosidase enzyme, preferably a thioglucosidase enzyme, and more preferably myrosinase. Myrosinase is also known as thioglucoside glucohydrolase.

In some embodiments, the composition comprises the enzyme in an amount of about 1 µg to about 1 µg, preferably about 50 µg to about 500 ng, and most preferably about 1 ng to about 150 ng. In some embodiments, compositions suitable for human use comprise about 5 ng to about 75 ng of the enzyme.

In some embodiments, the method comprises administering the enzyme, preferably myrosinase, in an amount of about 1 µg to about 1 µg, preferably about 50 µg to about 500 ng, and most preferably about 1 ng to about 150 ng. In some embodiments wherein the subject is a human, the method comprises administration of about 5 ng to about 75 ng of the enzyme. In some embodiments, the method comprises administering the enzyme to a subject in an amount of about 0.02 µg/kg to about 0.02 ug/kg, preferably about 0.7 µg/kg to about 7 ng/kg, and most preferably about 0.02 ng/kg to about 2 ng/kg. In some embodiments wherein the subject is a human, the method comprises administration of about 0.1 ng/kg to about 1 ng/kg. The above amounts may refer to each dosage administration or a total daily dosage.

In some embodiments, the method comprises administration of more than one enzyme capable of converting the sulforaphane precursor to sulforaphane. In some embodiments, the composition comprises more than one enzyme capable of converting the sulforaphane precursor to sulforaphane. In some embodiments wherein the methods or compositions comprise more than one enzyme, the above amounts may refer to the amount of each enzyme, or the total amount of the enzymes.

The present invention also provides for the use of a broccoli extract and/or powder, including but not limited to broccoli seed and sprout extracts and powders. The present invention provides methods of administration of broccoli extract and/or powder, and compositions comprising broccoli extract and/or powder. In some embodiments, the broccoli extract or powder is standardized to contain about 1% to about 75% w/w, more preferably about 2.5% to about 50%, even more preferably about 5% to about 25%, and most preferably about 10% to about 20% of a sulforaphane precursor, preferably glucoraphanin. Examples of broccoli extracts and powders include but are not limited to those described in U.S. Pat. Nos. 5,411,986; 5,725,895; 5,968,505; 5,968,567; 6,177,122; 6,242,018; 6,521,818; 7,303,770, and 8,124,135, each of which is incorporated by reference in its entirety. Powders of broccoli may be obtained, for example, by air drying, freeze drying, drum drying, spray drying, heat drying and/or partial vacuum drying broccoli, preferably broccoli sprouts. In some embodiments, the compositions and methods comprise use of about 1 µg to about 10 g, more preferably about 250 µg to about 5 g, even more preferably about 500 µg to about 1 g, preferably about 600 µg to about 500 mg, more preferably about 750 µg to about 400 mg, and most preferably about 1 mg to about 300 mg of the broccoli extract. In some embodiments, the broccoli extract or powder is present in a composition or administered to a subject in amounts sufficient to provide a sulforaphane precursor or sulforaphane in the amounts described above. In some embodiments, the composition may further comprise an enzyme potentiator, preferably ascorbic acid. In some embodiments, the method may further comprise administration of an enzyme potentiator, preferably ascorbic acid.

The sulforaphane or a derivative thereof, the sulforaphane precursor, and/or the enzyme capable of converting the sulforaphane precursor to sulforaphane may be obtained from any source, including but not limited to one or more plants from the Brassicaceae (also known as Cruciferae) family or one or more plants from the Moringaceae genus. Examples of plants from the Brassicaceae family include, but are not limited to, the following: broccoli, Brussels sprouts, cauliflower, cabbage, horseradish, parsnip, radish, wasabi, watercress, and white mustard. In some embodiments, sulforaphane precursor, preferably glucoraphanin, and the enzyme, preferably myrosinase, are obtained from broccoli, broccoli sprouts, or broccoli seeds. In some embodiments, the enzyme, preferably myrosinase, is obtained from *Moringa* plant components. The sulforaphane precursor and the enzyme may be obtained from the same source or from different sources. In some embodiments, both the sulforaphane precursor and the enzyme may be obtained from an extract or powder from a broccoli seed or sprout extract or powder. In some embodiments, the enzyme may be obtained from *Moringa* plant components.

The present invention provides for the use of an enzyme potentiator. Enzyme potentiators may be used to enhance the activity of the enzyme that is capable of converting the sulforaphane precursor to sulforaphane. In some embodiments, the enzyme potentiator comprises an enzyme cofactor, preferably ascorbic acid. Ascorbic acid, also known as ascorbate or vitamin C, can potentiate the activity of myrosinase. In some embodiments, without an enzyme potentiator such as ascorbic acid, the conversion reaction to sulforaphane may be too slow to occur in the location needed for peak absorption. The enzyme potentiator may be obtained from a natural source, or it may be produced synthetically.

In some embodiments, the compositions may comprise about 1 mg to about 500 mg, preferably about 1 mg to about 250 mg, and most preferably about 1 mg to about 125 mg of the enzyme potentiator. In some embodiments, compositions suitable for human use comprise about 1 mg to about 50 mg of the enzyme potentiator.

In some embodiments, the method of the present invention comprises administration of an enzyme potentiator, preferably ascorbic acid, in an amount of about 1 mg to about 500 mg, preferably 1 mg to about 250 mg, and most preferably about 1 mg to about 125 mg. In some embodiments wherein the subject is a human, the method comprises administration of about 1 mg to about 50 mg. In some embodiments, the method of the present invention comprises administration of the enzyme potentiator, preferably ascorbic acid, in an amount of about 0.01 mg/kg to about 3 mg/kg, and most about 0.02 mg/kg to about 2 mg/kg. In some embodiments wherein the subject is a human, the method comprises administration of about 0.02 mg/kg to about 0.7 mg/kg of the enzyme potentiator. The above amounts may refer to each dosage administration or a total daily dosage.

In some embodiments, the method comprises administration of more than one enzyme potentiator. In some embodiments, the composition comprises more than one enzyme potentiator. In some embodiments wherein the method or composition comprises more than one enzyme potentiator, the above amounts may refer to the amount of each enzyme potentiator, or the total amount of the enzyme potentiators.

In embodiments, the composition includes sulforaphane, a sulforaphane precursor, and/or a sulforaphane derivative with one or more *Moringa* plant components. Among other benefits, *Moringa* plant components provide a source of O-Ethyl-4-(α-L-rhamnosyloxy)benzyl carbamate, 4(α-L-rhamnosyloxy)-benzyl isothiocyanate, niazimicin, 3-O-(6'-O-oleoyl-β-D-glucopyranosyl)-β-sitosterol, and niaziminin. *Moringa* plant components as used in this invention can be derived from or consist of the *Moringa* leaves, seeds, fruits, fruit pods, roots, flowers, and/or bark, and any extract, powder, juice, or other derivative thereof. The invention includes, moreover, compositions which contain mixtures or combinations of *Moringa* plant components or respective derivatives. For example, the *Moringa* leaves, seeds, fruits, fruit pods, roots, flowers, and/or bark can be air dried, freeze dried, drum dried, spray dried, heat dried and/or partial vacuum dried in a hygienic area and then ground into a powder, including in a cold commercial grinding process. This cold commercial process protects the plant's antioxidant and anti-inflammatory properties from oxygen, light, and heat by cryogenically milling the plant materials. Extracts from the leaf, fruit, fruit pod, seed, root, flower, and/or bark can be prepared using any conventional extraction methods, including any suitable solvent and/or temperature regime. The fruit, fruit pods, or leaves can also be juiced to obtain the fruit juice, including by methods such as commercial juicing or squeezing processes. The seeds can also be harvested from the tree when they are mature and the oil can be removed through conventional practices, including commercial squeezing or extraction methods that avoid heat, light and oxygen to prevent damaging the vitamins, minerals, antioxidants and anti-inflammatory properties found in the seed solids, including cold press extraction methods. The present invention can also utilize the seed cake of the *Moringa* species, which is the byproduct of the process of seed pressing in order to extract the seed oil. This process keeps the vitamins, minerals and other active ingredients chemically undamaged during processing. The *Moringa* plant components as described above can then be further processed through mixing. *Moringa* plant components and combinations and mixtures thereof described above are all intended to be included within the present invention. Thus, in some embodiments, the composition and/or method of the present invention comprises a use of one *Moringa* plant component. In some embodiments, the composition and/or method of the present invention comprises a use of one or more *Moringa* plant components. In some embodiments, the composition and/or method of the present invention comprises a use of a powder, an extract, a juice, an oil, or a seed cake, or a mixture or combination thereof.

It has been found that glucomoringin is the predominant glucosinolate contained in *moringa* leaf extract. Through a hydrolysis transformation reaction, the enzyme myrosinase converts glucomoringin to the bioactive isothiocyanate 4-[(α-1-rhamnosyloxy)benzyl]isothiocyanate (moringin). Isothiocyanates are chemicals that are able to induce the production of Nrf-2-regulated Phase 2 enzymes which 1.) promote the metabolism and excretion of toxins and 2.) provide antioxidant activity. Additionally, isothiocyanates exert anti-inflammatory activity via the inhibition of the NFκ-ß pathway. *Moringa* leaf extract (MLE) typically contains 10 mg of moringin per gram.

In some embodiments, the compositions may comprise about 0.5 mg to about 2000 mg, about 1 mg to about 1000 mg, preferably about 1 mg to about 500 mg of one *Moringa* plant component. In some embodiments, the compositions may comprise about 1 mg to about 1750 mg, preferably about 100 mg to about 1000 mg, or 150 mg to 1500 mg of one or more *Moringa* plant components. The above amounts may refer to each dosage administration or a total daily dosage. Preferably, the compositions comprise the above amounts of *Moringa* leaf extract, and the *Moringa* leaf extract contains 10 mg or 14 mg of moringin per 1000 mg of *Moringa* leaf extract.

In another embodiment, the present invention may also include the use of a mushroom extract or powder. In some embodiments, the mushrooms may comprise "medicinal mushrooms," including, but not limited to maitake, shiitake, reishi, cremini, almond, chestnut, wood ear, cloud ear, porcini, ink cap, yarta gunbu, enokitake, shemeji, tiger milk, morel, bamboo, golden oyster, pink oyster, king oyster, hiratake, cauliflower, white jelly, golden jelly, matsutake, Mexican truffle, and straw mushrooms. In some embodiments, the mushroom comprises maitake mushroom, shiitake mushroom, reishi mushroom, and/or a mixture of one or more of these. Exemplary, though non-limiting, examples of suitable formulations are presented in U.S. Published Patent Appl. Nos. 2015/0147352 to Cornblatt et al. and 2015/0110872 to Cornblatt et al., each of which is incorporated in its entirety herein by reference.

Maitake mushroom belongs to the species *Grifola frondosa*. Maitake mushroom may contain a number of fractions having biological activity. Examples of components found in maitake mushroom include, but are not limited to: glucans (such as alpha-glucans and beta-glucans); lipids (such as octadecanoic and octadecadienoic acids); phospholipids (such as phosphatidylethanolamine, phosphatidylcholine, phosphatidylinositol, phosphatidylserine and phosphatidic acid).

Shiitake mushroom belongs to the species *Lentinula edodes*. Shiitake mushroom may contain a number of fractions having biological activity. Examples of components found in shiitake mushrooms include, but are not limited to, glucans (such as alpha-glucans and beta-glucans), proteins (such as lentin); lipids (such as linoleic acid); and lignins.

Reishi mushrooms belong to the species *Ganoderma lucidum*. Reishi mushrooms may contain a number of fractions having biological activity. Examples of components found in reishi mushroom include, but are not limited to: glucan (such as alpha-glucans and beta-glucans), canthaxanthin, sterols, coumarin, ganoderic acid, and mannitol.

In some embodiments, the mushroom extract or powder comprises one or more glucans. A glucan is a polysaccharide of a D-glucose monomer linked by glycosidic bonds and may be in the alpha or beta form. In some embodiments, the glucan comprises one or more alpha-glucan and/or beta-glucans. Alpha-glucans include, but are not limited to, 1,4-.alpha.-glucans and 1,6-.alpha.-glucans and beta-glucans include, but are not limited to, 1,3-.beta.-glucans, 1,4-.beta.-glucans, and 1,6-.beta.-glucans. The glucans may be expressed in a variety of polymeric configurations. In one embodiments, the maitake mushroom extract or powder comprises 1,3-.beta.-glucans and/or 1,6-.beta.-glucans. In another embodiments, the shiitake mushroom extract or powder comprises 1,4-.alpha.-glucans. In other embodiments, the reishi mushroom extract or powder comprises 1,3-.beta.-glucans and/or 1,6-.beta.-glucans. In some embodiments, the compositions and methods of the present invention may comprise use of glucans in a purified form or glucans produced synthetically, instead of a mushroom extract or powder.

In some embodiments, a maitake mushroom extract or powder may be used. In some embodiments, the maitake mushroom extract or powder is standardized to contain about 1% to about 75%, more preferably about 5% to about 50%, even more preferably about 10% to about 30%, and most preferably about 15% to about 20% of one or more glucans, preferably beta-glucans, and more preferably 1,3-beta glucan and/or 1,6-beta-glucan. Examples of maitake mushroom extracts and powders include, but are not limited to, those described in U.S. Pat. No. 5,854,404; WO 2007142130; EP 0893449; WO2009063885; WO2006107208; WO2007024496; and WO2001054673, each of which is incorporated by reference in its entirety. Powders of maitake mushroom may be obtained, for example, by air drying, freeze drying, drum drying, spray drying, heat drying and/or partial vacuum drying maitake mushrooms. In some embodiments, the composition comprises about 250 μg to about 100 mg, preferably about 500 μg to about 75 mg, and most preferably about 750 μg to about 50 mg. In some embodiments, compositions suitable for humans comprise about 1 mg to about 20 mg of maitake mushroom extract. In some embodiments, the method comprises administration of about 250 μg to about 100 mg, preferably about 500 μg to about 75 mg, and most preferably about 750 μg to about 50 mg. In some embodiments wherein the subject is human, the method comprises administration of about 1 mg to about 20 mg of maitake mushroom extract. The above amounts may refer to each dosage administration or a total daily dosage.

In some embodiments, a shiitake mushroom extract or powder may be used. In some embodiments, the shiitake mushroom extract or powder is standardized to contain about 1% to about 75%, preferably about 10% to about 60%, even more preferably about 25% to about 50%, and most preferably about 30% to about 40% of one or more glucans, preferably alpha-glucans, and more preferably 1,4-alpha-glucan. Examples of shiitake mushroom extracts include, but are not limited to, those described in U.S. Pat. Nos. 5,780,097; 6,582,723; WO2005107496, WO2007024496, and WO2000033069, each of which is incorporated by reference in its entirety. Powders of shiitake mushroom may be obtained, for example, by air drying, freeze drying, drum drying, spray drying, heat drying and/or partial vacuum drying shiitake mushrooms. In some embodiments, the composition comprises about 1 mg to about 1 g, preferably about 10 mg to about 500 mg, and most preferably about 25 mg to about 300 mg. In some embodiments, compositions suitable for humans comprise about 50 mg to about 250 mg of shiitake mushroom extract or powder. In some embodiments, the method comprises administration of about 1 mg to about 1 g, preferably about 10 mg to about 500 mg, and most preferably about 25 mg to about 300 mg. In some embodiments wherein the subject is human, the method comprises administration of about 50 mg to about 250 mg of shiitake mushroom extract or powder to a subject. The above amounts may refer to each dosage administration or a total daily dosage. The above amounts may refer to each dosage administration or a total daily dosage.

In some embodiments, a reishi mushroom extract or powder may be used. In some embodiments, the reishi mushroom extract comprises about 1% to about 75%, more preferably about 5% to about 50%, even more preferably about 10% to about 30%, and most preferably about 15% to about 20% of one or more glucans, preferably beta-glucans, and more preferably 1,3-beta glucan and/or 1,6-beta-glucan. Powders of reishi mushroom may be obtained, for example, by air drying, freeze drying, drum drying, spray drying, heat drying and/or partial vacuum drying reishi mushrooms.

In some embodiments, the composition and/or method comprises use of one type or mushroom extract or powder, such as maitake mushroom extract or powder, shiitake mushroom extract or powder or reishi mushroom extract or powder. In some embodiments, the composition and/or method comprises use of a mixture of one or more types of mushroom extract or powder. In some embodiments, the composition and/or method comprises use of a mixture of one or more of the following: maitake mushroom extract or powder, shiitake mushroom extract or powder, and reishi mushroom extract or powder. The composition and method may comprise use of an extract or a powder, or a mixture of extracts and powders.

The present invention also provides for the use of any glucan-rich component in place of, or in addition to, the mushroom extract or powder. Without intending any limitation, an example of a glucan-rich component is Baker's yeast. In some embodiments, yeast preparations may be used. In some embodiments, the yeast preparation comprises about 0.1% to about 50%, preferably about 0.5% to about 25%, and most preferably about 0.5% to about 10% of one or more glucans. Examples of yeast preparations include those discussed in U.S. Pat. Nos. 5,223,491 and 5,576,015, each of which is incorporated by reference in its entirety.

The methods of the present invention may further comprise administration of one or more additional components. The compositions of the present invention may further comprise one or more additional components. The additional components may include active pharmaceutical ingredients, nutritional supplements, and nutritional extracts. Examples of additional components include, but are not limited, ursolic acid, quercetin or a derivative thereof, an aminosugar such as glucosamine, a glycosaminoglycan such as chondroitin, avocado/soybean unsaponifiables, vitamins such as vitamin K2, coffee fruit, magnesium, ursolic acid, proanthocyanidins, alpha- and beta-glucans, curcumin, phytosterols, phytostanols, and S-adenosylmethionine (SAMe). These additional components may be present in milk thistle (*Silybum marianum*) extract (silymarin), turmeric (*Curcuma longa*).

In some embodiments, the ratio of beta-glucan to sulforaphane or a derivative thereof (beta-glucan:sulforaphane or a derivative thereof) is about 50:1 to about 1:50, preferably about 25:1 to about 1:25, more preferably about 10:1 to about 1:20, more preferably about 5:1 to about 1:10, even more preferably about 1:1 to about 1:8, and most preferably about 1:3 to about 1:5. In some embodiments, the ratio of alpha-glucan to sulforaphane or a derivative of (alpha-glucan:sulforaphane or a derivative of) is about 1:50 to about 50:1, preferably about 1:10 to about 25:1, more preferably about 1:5 to about 20:1, more preferably about 1:1 to about 15:1, even more preferably about 2:1 to about 10:1, and most preferably about 3:1 to about 8:1. In some embodiments, the ratio of beta-glucan to sulforaphane precursor of (beta-glucan:sulforaphane precursor) is about 50:1 to about 1:50, preferably about 30:1 to about 1:35, more preferably about 20:1 to about 1:25, more preferably about 10:1 to about 1:20, even more preferably about 5:1 to about 1:15, and most preferably about 1:1 to about 1:10. In some embodiments, the ratio of alpha-glucan to precursor (alpha-glucan:precursor) is about 1:50 to about 100:1, preferably about 1:25 to about 75:1, more preferably about 1:10 to about 50:1, more preferably about 1:5 to about 40:1, even more preferably about 1:1 to about 30:1, and most preferably about 2:1 to about 20:1.

In some embodiments, the composition comprises a unit dosage form, including but not limited to pharmaceutical dosage forms suitable for oral, rectal, intravenous, subcutaneous, intramuscular, transdermal, transmucosal, and topical. In some embodiments, the composition comprises an orally administrable dosage form or a rectally administrable dosage form. Examples of orally administrable dosage forms include, but are not limited to a tablet, capsule, powder that can be dispersed in a beverage, a liquid such as a solution, suspension, or emulsion, a soft gel/chew capsule, a chewable bar, or other convenient dosage form known in the art. In embodiments, the composition comprises a tablet, capsule, or soft chewable treat. The orally administrable dosage forms may be formulated for immediate release, extended release or delayed release.

In some embodiments, at least the sulforaphane precursor, the enzyme, and the enzyme potentiator are provided in a dosage form which allows for the release in an area of the gastrointestinal tract having a pH of at least 4 and preferably at least 5, such as the small intestine, preferably the duodenum. In some embodiments, at least the sulforaphane or derivative thereof and/or the broccoli extract or powder are provided in a dosage form which allows for the release in an area of the gastrointestinal tract having a pH of at least 4 and preferably at least 5, such as the small intestine, preferably the duodenum. In some embodiments, the mushroom extract or powder and/or any optional additional components are also released in an area of the gastrointestinal tract having a pH of at least 4 and preferably at least 5, such as the small intestine, preferably the duodenum. The small intestine includes the duodenum, jejunum, and ileum.

In some embodiments, each of these components (i.e, sulforaphane precursor, enzyme, enzyme potentiator, sulforaphane or a derivative thereof, broccoli extract or powder, mushroom extract or powder, and/or additional components) are released simultaneously or concomitantly (i.e., within a short period of time of each other). This provides benefits over glucoraphanin-containing compositions formulated to release the glucoraphanin in an area of the gastrointestinal tract having a pH below 4, such as the stomach. In low pH environments such as this, the acidic environment may divert conversion of sulforaphane precursor to other, physiologically inactive end products, such as sulforaphane nitrile and epithionitrile.

In some embodiments, the compositions may comprise orally administrable compositions which comprise enteric coated dosage forms or any dosage form which is resistant to degradation in an area of the gastrointestinal tract having pH below 4, such as the stomach. For example, the orally administrable composition may comprise a tablet or capsule comprising an enteric coating. The enteric coating may comprise materials including, but not limited to cellulose acetate phthalate, hydroxypropyl methylcellulose phthalate, polyvinyl acetate phthalate, methacrylic acid copolymer, methacrylic acid:acrylic ester copolymer, hydroxypropyl methylcellulose acetate succinate, hydroxypropyl methylcellulose trimellitate, shellac, cellulose acetate trimellitate, carboxymethylethylcellulose, and mixtures thereof. The enteric coating may comprise any suitable enteric polymers known in the art. In some embodiments, one or more of the components in the composition may be embedded in a matrix of enteric polymers. In some embodiments, the orally administrable compositions comprise a capsule that dissolves slowly in gastric acid and travels to the small intestine, such as DRCAPS® acid resistant capsules, which are marketed by CAPSUGEL®, or any other acid resistant capsules.

In one form, the orally administrable composition is surrounded by a coating that does not dissolve unless the surrounding medium is at a pH of at least 4, and more preferably at least 5. Alternatively, a coating may be employed which controls the release by time, as opposed to pH, with the rate adjusted so that the components are not released until after the pH of the gastrointestinal tract has risen to at least 4, and more preferably at least 5. Thus, a time-release formulation may be used to prevent gastric presence of the sulforaphane precursor, the enzyme capable of converting the sulforaphane precursor to sulforaphane, and the enzyme potentiator, or of the sulforaphane. The coating layer(s) may be applied onto orally administrable composition using standard coating techniques. The enteric coating materials may be dissolved or dispersed in organic or aqueous solvents. The pH at which the enteric coat will dissolve can be controlled by a polymer, or combination of polymers, selected and/or ratio of pendant groups. For example, dissolution characteristics of the polymer film can be altered by the ratio of free carboxyl groups to ester groups. Enteric coating layers also contain pharmaceutically acceptable plasticizers such as triethyl citrate, dibutyl phthalate, triacetin, polyethylene glycols, polysorbates or other plasticizers. Additives such as dispersants, colorants, anti-adhering and anti-foaming agents may also be included.

The compositions may contain one or more non-active pharmaceutical ingredients (also known generally as "excipients"). Non-active ingredients, for example, serve to solubilize, suspend, thicken, dilute, emulsify, stabilize, preserve, protect, color, flavor, and fashion the active ingredients into an applicable and efficacious preparation that is safe, convenient, and otherwise acceptable for use. The excipients are preferably pharmaceutically acceptable excipients. Examples of classes of pharmaceutically acceptable excipients include lubricants, buffering agents, stabilizers, blowing agents, pigments, coloring agents, flavoring agents, fillers, bulking agents, fragrances, release modifiers, adjuvants, plasticizers, flow accelerators, mold release agents, polyols, granulating agents, diluents, binders, buffers, absorbents, glidants, adhesives, anti-adherents, acidulants, softeners, resins, demulcents, solvents, surfactants, emulsifiers, elastomers and mixtures thereof.

In some embodiments, the combination of (i) a sulforaphane precursor, preferably glucoraphanin, (ii) an enzyme capable of converting the sulforaphane precursor to sulforaphane, preferably a glucosidase enzyme, more preferably a thioglucosidase enzyme, and most preferably myrosinase, (iii) an enzyme potentiator, preferably an enzyme co-factor, more preferably ascorbic acid, and (iv) a mushroom extract or powder (which contains glucans) demonstrates a synergistic effect. In some embodiments, the combination of sulforaphane (or a derivative thereof) and a mushroom extract or powder (which contains glucans) demonstrates a synergistic effect. Synergy refers to the effect wherein a combination of two or more components provides a result which is greater than the sum of the effects produced by the agents when used alone. In some embodiments, the synergistic effect is greater than an additive effect. In some embodiments, the combination of a sulforaphane precursor, an enzyme capable of converting the sulforaphane precursor to sulforaphane, an enzyme potentiator, and a maitake, shiitake, or reishi mushroom extract or powder has a statistically significant, greater effect compared to: (i) each component alone, (ii) the combination of sulforaphane precursor and the enzyme alone; and/or (iii) the combination of sulforaphane precursor, the enzyme, and the enzyme potentiator alone.

In some embodiments, the combination of the sulforaphane precursor, the enzyme, the enzyme potentiator, and a mushroom extract or powder (which contains glucans) demonstrates synergy by having a statistically significant and/or greater than additive effect compared to the sulforaphane precursor alone and the mushroom extract or powder alone. In some embodiments, the combination of glucoraphanin, myrosinase, ascorbic acid, and a mushroom extract or powder has a synergistic effect compared to the combination of glucoraphanin, myrosinase, ascorbic acid alone; and compared to glucans alone.

In some embodiments, the combination of a sulforaphane (or a derivative thereof) and a mushroom extract or powder has a statistically significant and/or greater than additive effect than: (i) sulforaphane (or a derivative thereof) alone, and/or (ii) a mushroom extract or powder alone. In some embodiments, the combination of sulforaphane and glucan has a synergistic effect compared to sulforaphane alone, and glucan alone.

In some embodiments, the combination of broccoli extract or powder and a mushroom extract or powder has a statistically significant and/or greater than additive effect than: (i) broccoli extract or powder alone, and/or (ii) a mushroom extract or powder alone. In some embodiments, the combination of broccoli extract or powder and glucan has a synergistic effect compared to broccoli extract or powder alone, and glucan alone.

The present invention provides methods of use, including methods of administration to a subject in need thereof. In some embodiments, the method comprises administration of the combination of a sulforaphane precursor, an enzyme capable of converting the sulforaphane precursor to sulforaphane, an enzyme potentiator, and a mushroom extract or powder. In some embodiments, the method comprises administration of the combination of a sulforaphane or a derivative thereof and a mushroom extract or powder. In some embodiments, the method comprises administration of the combination of a broccoli extract or powder and a mushroom extract or powder.

In some embodiments, the method relates to treating, preventing, reducing the occurrence of, decreasing the symptoms associated with, and/or reducing secondary recurrences of, cancer, in particular breast cancer, prostate cancer, colon cancer, lung cancer, liver cancer, and bladder cancer in a subject. The methods may be useful in reducing damage or slowing damage to tissues and organs, such as the breast, prostate, colon, lung, liver, and bladder. The present invention provides methods of treating, preventing, decreasing the symptoms associated with, and/or reducing secondary recurrences of diseases and conditions associated with the reproductive system (including but not limited to the breast and prostate), colon, liver, bladder, kidney, central nervous system, cardiovascular system, pulmonary system, genitourinary system, hematopoietic system, and joints. The present invention also provides for methods of treating, preventing, decreasing the symptoms associated with, and/or reducing secondary recurrences of cysts, such as benign cysts.

In some embodiments, the method relates to increasing levels or increasing gene expression of NAD(P)H:quinone oxidoreductase 1 (NQO-1) in a subject. The method may also be useful in treating, preventing, decreasing the symptoms associated with, and/or reducing secondary recurrences of diseases and conditions which would be benefited from an increase in gene expression or levels of NQO-1. Examples of such diseases and conditions include, but are not limited to cancer, myelodysplastic syndrome, cardiovascular disease, and tardive dyskinesia.

In some embodiments, the method relates to treating, preventing, reducing the occurrence of, decreasing the symptoms associated with, and/or reducing secondary recurrences of a disease or condition associated with elevated levels of quinone estrogen. Examples of such diseases and conditions include, but are not limited to cancer, myelodysplastic syndrome, cardiovascular disease, and tardive dyskinesia.

In some embodiments, the methods relate to providing a beneficial effect on biomarkers, and treating, preventing, reducing the occurrence of, decreasing the symptoms associated with abnormal levels of these biomarkers. Examples of such biomarkers include, but are not limited to NADPH-dependent enzymes, thioredoxin (TXN), thioredoxin reductase-1 (Txnrd-1), glutamate-cysteine ligase subunit (GCLC), sulfotransferase 1A1 (SULT1A1), heme oxygenase-1 (HMOX1), glutathione peroxidase-3 (GPx-3), glutathione S-transferase theta 2 (GSTT2), microsomal glutathione S-transferase 1 (MGST1), aldehyde oxidase (AOX1), aldo-keto reductase 1 B8 (Akr1 b8), flavin-containing monooxygenase 2 (FMO2), Fc receptor region receptor III (Fcgr3), tryptase beta 1 (TPSB1), mast cell protease-6 (Mcpt6), neurexin-1-alpha (NRXN-1), microphthalmia-associated transcription factor (MITF), type II iodothyronine deiodinase (DIO2), angiopoietin-14 (Angpt14), cluster of differentiation (CD36), and Ntel. Diseases or conditions associated with elevated or abnormal levels of these biomarkers include, but are not limited to cancer, pulmonary and central nervous system tuberculosis, multiple sclerosis, Crohn's disease, atherosclerosis, osteoarthritis, asthma, stroke, emphysema, diabetic nephropathy, chronic histiocytic intervillositis of the placenta, hypertension, abdominal aortic aneurysm, inflammatory bowel disease, chronic rhinosinusitis, coronary artery disease, and kidney disease.

In some embodiments, the method comprises administering to a subject in need thereof a combination of sulforaphane and a mushroom extract or powder containing glucan. In some embodiments the method comprises administering to a subject in need thereof a combination of broccoli extract or powder and a mushroom extract or powder containing glucan. In some embodiments, the method comprises administering to the subject a combination of glucoraphanin, myrosinase, ascorbic acid, and a mushroom extract or powder containing glucan. In some embodiments, the combinations demonstrate a synergistic effect in the methods of the present invention.

In some embodiments, the method comprises administering to a subject in need thereof a combination of sulforaphane, a mushroom extract or powder, and one or more *Moringa* plant components. In some embodiments the method comprises administering to a subject in need thereof a combination of broccoli extract or powder, a mushroom extract or powder, and one or more *Moringa* plant components. In some embodiments, the method comprises administering to the subject a combination of glucoraphanin, myrosinase, ascorbic acid, a mushroom extract or powder, and one or more *Moringa* plant components.

In some embodiments, one or more components of the combinations (for example, the sulforaphane precursor, the enzyme capable of converting the sulforaphane precursor to sulforaphane, the enzyme potentiator, the mushroom extract or powder; or the sulforaphane or derivative thereof and the mushroom extract or powder; or the broccoli extract or powder and the mushroom extract or powder); one or more *Moringa* plant components, are administered together in one composition or dosage form, or separately, preferably within a period in which their therapeutic properties overlap. In some embodiments, the components of the combinations may be administered in two or more orally administrable compositions or dosage forms. For example, in some embodiments, the sulforaphane precursor, the enzyme capable of converting the sulforaphane precursor to sulforaphane, and the enzyme potentiator are administered in one orally administrable dosage form, while a mushroom extract or powder are administered in one or more separate or additional orally administrable dosage form(s). In some embodiments, the components of the combination are administered in one dosage form.

In some embodiments, the combination may be administered at a frequency of 1 to 10 times daily, preferably 1 to 5 times daily, more preferably 1 to 3 times daily, and most preferably 1 time daily.

The dosages disclosed in this application refer preferably to dosages suitable for humans. Dosage calculations can be determined by those of skilled in the art by evaluating body weight, surface area, metabolic rate, and species differences. Moreover, any desired dosage amount of any form of the compositions disclosed herein or derived therefrom may be given to any human or non-human animal and is within the scope of the present invention.

The term "subject" refers to any animal, including mammals and birds. Mammals include, but are not limited to, humans, dogs, cats, horses, cows, camels, elephants, lions, tigers, bears, seals, and rabbits. In some embodiments, the subjects comprise mammals that are not typically consumed as food, such as humans, cats, and dogs.

EXAMPLES

Example 1

Formulations

The following are exemplary formulation of the present invention. As described above, embodiments of the compositions include sulforaphane or a sulforaphane precursor with one or more *Moringa* plant components.

Formulation A

Glucoraphanin-containing broccoli seed extract (about 12% w/w), 50 mg to 5 grams Myrosinase-containing freeze-dried broccoli sprout powder, 25 mg to 500 mg Ascorbic acid, 1 mg to 50 mg Alpha Glucan-containing shiitake mushroom extract (about 40% w/w), 1 mg to about 1 g *Moringa* plant components.

Formulation B

Glucoraphanin-containing broccoli seed extract (about 12% w/w), 50 mg to 5 grams, Myrosinase-containing freeze-dried broccoli sprout powder, 25 mg to 500 mg Ascorbic acid, 1 mg to 50 mg Beta Glucan-containing maitake mushroom extract (about 20% w/w), 1 mg to about 1 g *Moringa* plant components.

Formulation C

Glucoraphanin-containing broccoli seed extract (about 12% w/w), 50 mg to 5 grams Myrosinase-containing freeze-dried broccoli sprout powder, 25 mg to 500 mg Ascorbic acid, 1 mg to 50 mg Alpha Glucan-containing shiitake mushroom extract (about 40% w/w), 1 mg to about 500 mg *Moringa* plant components.

Formulation D

Glucoraphanin-containing broccoli seed extract (about 12% w/w), 50 mg to 5 grams, Myrosinase-containing freeze-dried broccoli sprout powder, 25 mg to 500 mg Ascorbic acid, 1 mg to 50 mg Beta Glucan-containing maitake mushroom extract (about 20% w/w), 1 mg to about 500 mg *Moringa* plant components.

Formulation E

An orally administrable composition comprising:

Broccoli seed extract

Broccoli sprout extract

Maitake mushroom extract

*Moringa* plant components

Ascorbic acid fixed concentration of broccoli sprout-derived myrosinase in the presence of variable concentration of ascorbic acid, ranging from 0 to 600 µmoles/Liter. The reaction mixtures were thermostated at 38° C.; aliquots were withdrawn every 15 minutes for 60 minutes, and concentration of glucoraphanin determined chromatographically. The rate of glucoraphanin consumption was interpreted as the rate its conversion to sulforaphane. Graphical representation of glucoraphanin content reduction as a function of increasing ascorbic acid concentration results in a series of linear plots; the slopes of the linear regression lines reflect the rate of glucoraphanin consumption, in pmoles/minute. It is apparent that in the presence of 600 µmoles/Liter concentration of ascorbic acid, the reaction rate increased 13-fold relative to that which proceeded in the absence of modulatory effects of ascorbic acid.

| | Content of Ascorbic Acid | | | | | | | |
|---|---|---|---|---|---|---|---|---|
| Time, min | 0 µM | 50 µM | 125 µM | 250 µM | 250 µM Filtered | 400 µM | 600 µM | |
| 0 | 93.36 | 93.36 | 93.36 | 93.36 | 93.36 | 93.36 | 93.36 | µmoles |
| 15 | 92.24 | 89.20 | 84.52 | 80.95 | 86.31 | 78.32 | 75.02 | GR |
| 30 | 90.71 | 84.24 | 75.92 | 69.06 | 79.44 | 62.78 | 55.66 | |
| 45 | 89.44 | 80.30 | 68.09 | 57.63 | 71.94 | 47.67 | 37.50 | |
| 60 | 87.79 | 76.36 | 59.41 | 45.76 | 65.18 | 33.15 | 22.09 | |
| Slope | −0.09293 | −0.28599 | −0.56217 | −0.79012 | −0.47140 | −1.00714 | −1.20029 | µmol/min |
| intercept | 93.496 | 93.271 | 93.123 | 93.053 | 93.386 | 93.270 | 92.734 | µmol |

Hydroxypropylmethyl cellulose
Microcrystalline cellulose
Corn starch
Ethylcellulose
Croscarmellose sodium
Sodium starch glycolate
Crospovidone
Silicon dioxide
Sodium alginate
Medium chain triglycerides
Maltodextrin
Oleic Acid
Magnesium stearate
Stearic acid

Example 2

A Hydrophobic Interaction Chromatographic (HILIC) method was developed, comprising the following conditions:

Column: Waters BEH Amide, 1.7-µm particle size; 2.1 mm.times.100 mm;

Mobile Phase: 20% 10 mM Ammonium Acetate, pH 5.0; 80% acetonitrile;

Separation mode: isocratic;

Column Temperature: 70° C.;

Flow Rate: 0.7 mL/min.

The above conditions allow separation of five typical Brassicaceae glucosinolates, including the sulforaphane precursor, glucoraphanin.

Example 3

Consumption of Glucoraphanin as a Function of the Ascorbic Acid Concentration

About 250 mg of broccoli seed extract containing about 12% (w/w) glucoraphanin were subjected to hydrolysis by a

Example 4

Equimolar Conversion of Glucoraphanin to Sulforaphane

A two-part experiment was conducted to further elucidate the role of ascorbic acid in modulating myrosinase activity. All solutions were prepared in 20 mM Tris-buffered saline, at pH 7.5, previously identified as an optimal for myrosinase activity; each sample tube had 100 mg of freeze-dried broccoli powder accurately weighed in as a source of myrosinase. Experiment was conducted at 38° C. for 2 hours, with sample aliquots removed in 30-minute increments, and both glucoraphanin and sulforaphane content assessed by HPLC. A strongly acidic "stop" solution was utilized to instantaneously inhibit further myrosinase activity in the removed aliquots. A control sample contained no ascorbic acid, and the enzymatic conversion proceeded unassisted by a co-factor.

PART 1. In the presence of the fixed concentration of ascorbic acid, 1 mmol/Liter, an increasing amount of broccoli seed extract (about 12% glucoraphanin, w/w) was added, ranging from 250 mg to 500 mg.

PART 2. While keeping the amount of broccoli seed extract fixed at 250 mg, the concentration of ascorbic acid was varied from 0.4 mmol/Liter to 3.8 mmol/Liter.

Table 1 below presents glucoraphanin and sulforaphane expressed in pmoles. It is apparent that within the first 30 minutes in almost all the reaction mixtures, conversion of glucoraphanin to sulforaphane was complete. However, careful examination of the enzymatic conversion occurring in the control sample, without the stimulating effects of ascorbic acid, reveals an equimolar conversion of glucoraphanin to sulforaphane, i.e., the amount of glucoraphanin consumed results in the equivalent amount of sulforaphane produced.

TABLE 1

| Time, min | Glucoraphanin, μmoles | | | | | Sulforaphane, μmoles | | | | |
|---|---|---|---|---|---|---|---|---|---|---|
| | 0 | 30 | 60 | 90 | 120 | 0 | 30 | 60 | 90 | 120 |
| GR 250 mg AA 0.0 mM | 58.02 | 48.57 | 37.52 | 28.58 | 15.67 | 3.42 | 12.08 | 22.27 | 33.17 | 42.89 |
| GR 250 mg AA 1.0 mM | 40.07 | | | | | 21.51 | 61.95 | 60.20 | 60.04 | 58.25 |
| GR 300 mg AA 1.0 mM | 49.31 | | | | | 24.18 | 74.40 | 73.04 | 72.19 | 70.56 |
| GR 350 mg AA 1.0 mM | 61.41 | | | | | 25.00 | 84.92 | 84.02 | 83.19 | 80.02 |
| GR 400 mg AA 1.0 mM | 71.35 | 1.56 | | | | 26.71 | 96.60 | 95.38 | 93.39 | 91.16 |
| GR 500 mg AA 1.0 mM | 89.41 | 1.01 | | | | 33.52 | 120.16 | 116.45 | 118.45 | 112.34 |
| GR 250 mg AA 0.4 mM | 45.66 | | | | | 15.96 | 62.06 | 61.01 | 60.88 | 56.90 |
| GR 250 mg AA 1.0 mM | 35.24 | | | | | 26.49 | 62.19 | 60.62 | 60.41 | 59.10 |
| GR 250 mg AA 2.0 mM | 24.94 | | | | | 36.05 | 60.85 | 59.78 | 59.85 | 58.08 |
| GR 250 mg AA 2.9 mM | 22.24 | | | | | 38.20 | 59.95 | 59.34 | 58.77 | 56.99 |
| GR 250 mg AA 3.8 mM | 21.70 | | | | | 37.87 | 58.77 | 57.79 | 58.41 | 56.17 |

In Part 2 of the experiment, the modulatory effect of the increasing concentration of ascorbic acid on the activity of myrosinase was assessed. An initial, apparently linear, increase in myrosinase-promoted conversion of glucoraphanin to sulforaphane is observed to about 2 mmol/L of ascorbic acid concentration, followed subsequently by a considerable leveling off.

Finally, examination of sulforaphane yield of after 30 minutes within the PART 1 of the experiment, reveals that in the presence of 1 mmol/Liter of ascorbic acid, the fixed amount of myrosinase contained in 100 mg of freeze-dried broccoli sprout powder is capable of generating at least 200 μmoles of sulforaphane, in a predictably linear fashion. FIGS. 1, 2, 3, and 4 demonstrate the results of this study.

Example 5

Conversion of Glucoraphanin to Sulforaphane in the Presence of Simulated Intestinal Fluid Simulated Intestinal Fluid (SIF) powder, a commercially supplied concentrate closely approximating the human intestinal content in terms of composition, pH and ionic strength, was used. The experiment utilized a USP Dissolution Apparatus 2 (paddles), where into six dissolution vessels 500 mL of Simulated Intestinal Fluid was dispensed, along with 150 mg of freeze-dried broccoli sprout powder as a source of myrosinase. In vessels 1-4, the concentration of ascorbic acid was varied from 0.25 to 1.00 mmol/Liter; in vessel 5, in addition to 1 mmol/Liter ascorbic acid, 3.125 g of pancreatin (8.times.USP) was suspended; in vessel 6, in addition to 1 mmol/Liter ascorbic acid, and 3.125 g of pancreatin (8.times.USP), a doubled amount of freeze-dried broccoli sprout powder (300 mg) was added. After vessels were brought to 38° C., 250 mg of glucoraphanin-rich (12%, w/w) broccoli seed extract was added to each, and the resulting suspensions were stirred at 75 RPM for 2 hours. Aliquots were withdrawn every 15 minutes, and assayed for sulforaphane. FIG. 1 shows direct correlation between larger yield of sulforaphane and higher concentrations of ascorbic acid, especially at the earlier stages of the experiment.

Example 6

The following study was conducted to determine the effect of the combination of sulforaphane and a maitake mushroom extract containing 20% b-glucans on the gene expression of NAD(P)H:quinone oxidoreductase 1 (NQO1). NQO1 encodes a protein that is able to metabolize estrogen quinones, preventing them from forming DNA adducts that cause mutations and ultimately carcinogenesis. An increase in NQO1 expression is favorable for breast, colon, liver, lung, skin and prostate health. Further, NQO1 protein is a Phase II enzyme that promotes cellular health by catalyzing the two-electron reduction of quinone. This chemical reaction is important for cellular processes including benzene detoxification. During benzene detoxification, a Phase I enzyme converts benzene into reactive epoxides which can bind to DNA and lead to cancer-inducing mutations. NQO1 converts benzene intermediates into a hydroquinone which is less toxic and can be further metabolized prior to elimination from the body.

Figure 2:
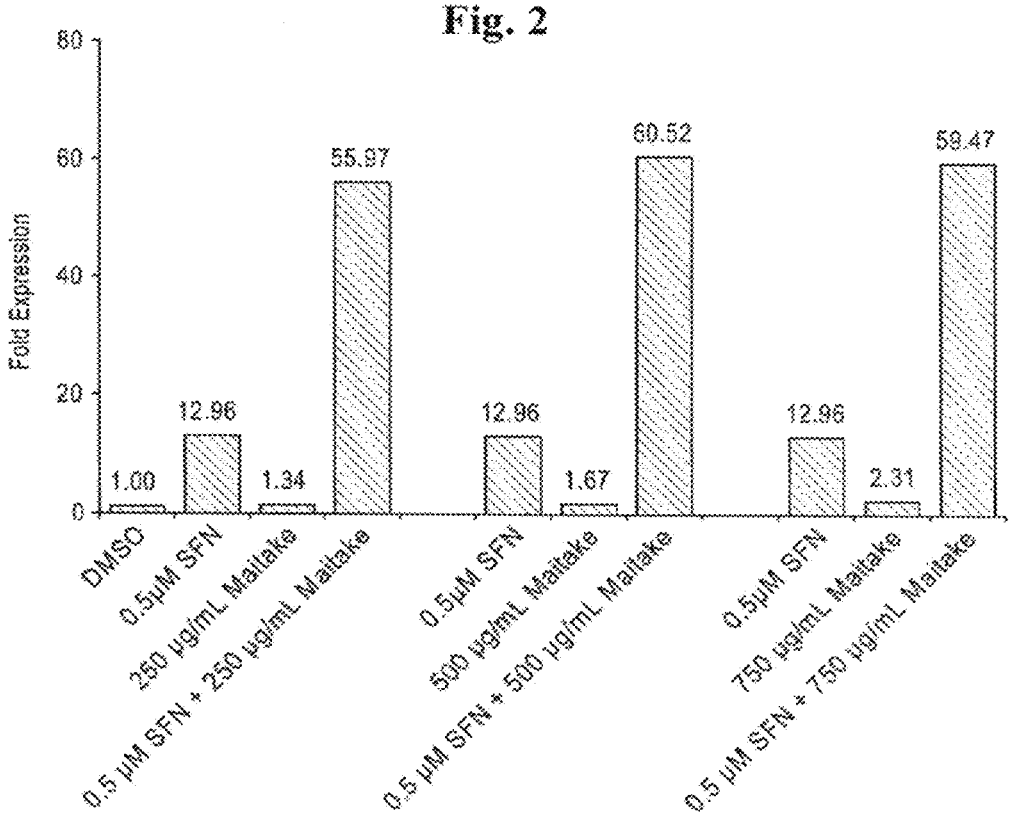
FIG. 2 is a graph showing the results of the experiment described in Example 6.

In the study, the macrophage cell line RAW 264.7 was treated with dimethyl sulfoxide (DMSO) (vehicle control), sulforaphane (SFN), a maitake mushroom extract having about 20% beta-glucan content (Maitake), or the combination of sulforaphane and the maitake mushroom extract, for 24 hours. In particular, the cells were treated with one of the following: (i) DMSO (vehicle control), (ii) 0.5 μM SFN, (iii) 250 μg/mL Maitake, (iv) 500 μg/mL Maitake, (v) 750 μg/mL Maitake, (vi) 0.5 μM SFN and 250 μg/mL Maitake, (vii) 0.5 μM SFN and 500 μg/mL Maitake, and (viii) 0.5 μM SFN and 750 μg/mL Maitake. The gene expression of NQO-1 was analyzed via quantitative RT-PCR. The results, which are depicted in FIG. 2, show the following:

| Treatment | Fold increase in NQO-1 gene expression |
|---|---|
| DMSO | 1.00 |
| 0.5 μM SFN | 12.96 |
| 250 μg/mL Maitake | 1.34 |
| 0.5 μM SFN + 250 μg/mL Maitake | 55.97 |
| 500 μg/mL Maitake | 1.67 |
| 0.5 μM SFN + 500 μg/mL Maitake | 60.52 |
| 750 μg/mL Maitake | 2.31 |
| 0.5 μM SFN + 750 μg/mL Maitake | 59.47 |

The results demonstrate that the combination of sulforaphane and the maitake mushroom extract had a synergistic effect compared to each component alone. This effect was found to be more than merely additive.

Example 7

The following study was conducted to determine the effect of the combination of sulforaphane and a shiitake mushroom extract containing 40% alpha glucans on the gene expression of NAD(P)H:quinone oxidoreductase 1 (NQO1).

In the study, the macrophage cell line RAW 264.7 was treated with DMSO (vehicle control), sulforaphane (SFN), a shiitake mushroom extract having at least 20% alpha-glucan content (Shiitake), or the combination of sulforaphane and

Figure 3:
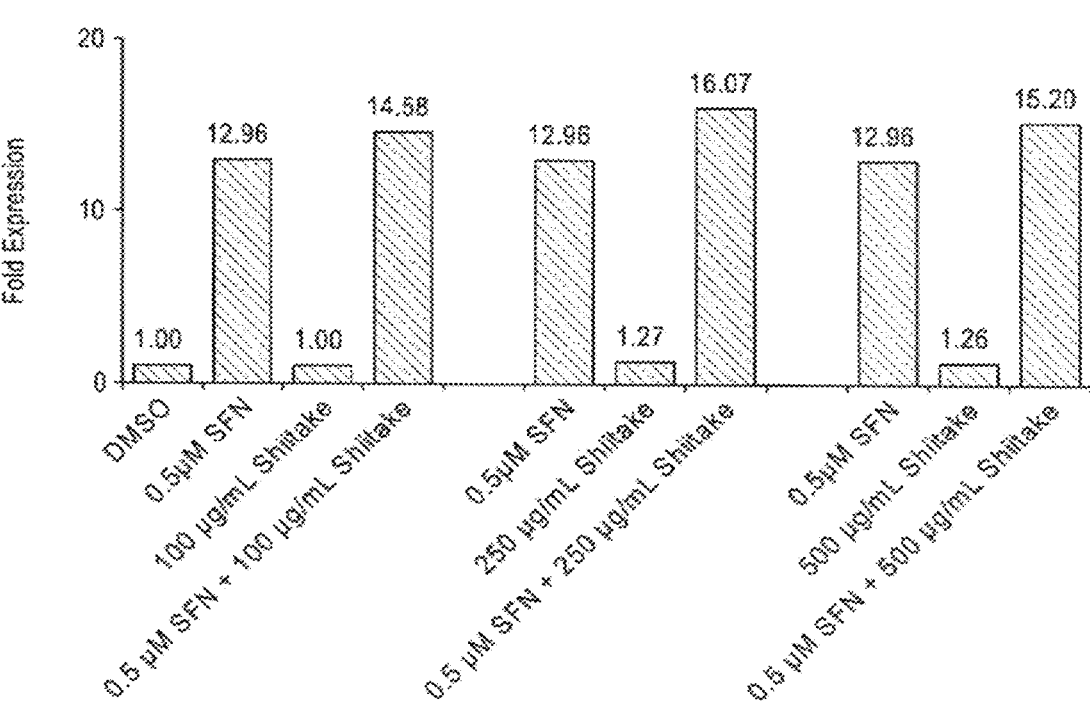
FIG. 3 is a graph showing the results of the experiment described in Example 7.

23 the shiitake mushroom extract, for 24 hours. In particular, the cells were treated with one of the following: (i) DMSO (vehicle control), (ii) 0.5 μM SFN, (iii) 100 μg/mL Shiitake, (iv) 250 μg/mL Shiitake, (v) 500 μg/mL Shiitake, (vi) 0.5 μM SFN and 100 μg/mL Shiitake, (vii) 0.5 μM SFN and 250 μg/mL Shiitake, and (viii) 0.5 μM SFN and 500 μg/mL Shiitake. The gene expression of NQO1 was analyzed via quantitative RT-PCR. The results, which are depicted in FIG. 3, show the following:

| Treatment | Fold increase in NQO-1 gene expression |
|---|---|
| DMSO | 1.00 |
| 0.5 μM SFN | 12.96 |
| 100 μg/mL Shiitake | 1.00 |
| 0.5 μM SFN + 100 μg/mL Shiitake | 14.58 |
| 250 μg/mL Shiitake | 1.27 |
| 0.5 μM SFN + 250 μg/mL Shiitake | 16.07 |
| 500 μg/mL Shiitake | 1.26 |
| 0.5 μM SFN + 500 μg/mL Shiitake | 15.20 |

The results demonstrate that the combination of sulforaphane and the shiitake mushroom extract had a synergistic effect compared to each component alone. This effect was found to be more than merely additive.

Example 8

The following study was conducted to determine whether the combination of *Moringa* leaf extract (MOR) and sulforaphane (SFN) have a synergistic effect on the induction of heme oxygenase-1 (HMOX1) gene expression.

The model system included cultured HepG2 hepatocellular carcinoma cells. It is noted that heme oxygenase 1 (HO-1)/HSP32 promotes cellular health by detoxifying oxidants and minimizing inflammation. HO-1 catalyzes the breakdown of heme resulting in the release of ferrous iron ($Fe^{2+}$), carbon monoxide (CO), and biliverdin. Biliverdin is further broken down into bilirubin. These by-products afford HO-1 with antioxidant, anti-inflammatory, antiapoptotic, antiproliferative, and immunomodulatory properties.

In this in vitro study, human hepatocellular carcinoma HepG2 cells were treated with either sulforaphane (SFN), *Moringa* plant components (MOR), or a combination of SFN and MOR, for 6 hours. In particular, the cells were treated with one of the following: (i) 0 μg/mL MOR and 0 μM SFN (control), (ii) 1.375 μg/mL MOR, (iii) 0.1 μM SFN, (iv) 0.25 μM SFN, (v) 0.5 μM SFN, (vi) 1.375 μg/mL MOR and 0.1 μM SFN, (vii) 1.375 μg/mL MOR and 0.25 μM SFN, (viii) 1.375 μg/mL MOR and 0.5 μM SFN, (ix) 2.75 μg/mL MOR, (x) 2.75 μg/mL MOR and 0.1 μM SFN, (xi) 2.75 μg/mL MOR and 0.25 μM SFN, (xii) 2.75 μg/mL MOR and 0.5 μM SFN, (xiii) 5.5 μg/mL MOR, (xiv) 5.5 μg/mL MOR and 0.1 μM SFN, (xv) 5.5 μg/mL MOR and 0.25 μM SFN, and (xvi) 5.5 μg/mL MOR and 0.5 μM SFN. Cells were collected, RNA was extracted and HMOX1 gene expression was assessed via RT-PCR.

All the combinations of MOR and SFN induced the expression of HMOX1 more than either individual component alone. Synergy was achieved with these combinations.

Example 9

A subject presents with breast cancer and is suffering from symptoms including damaged breast tissue and breast pain. She is administered a tablet containing glucoraphanin, myrosinase, ascorbic acid, and a maitake mushroom extract. The tablet is an enteric coated formulation which releases the contents in the small intestine. After one month of daily administration of the tablet, the subject experiences modulation of surrogate biomarkers including NQO1 which correlate with improved in symptoms.

Example 10

A subject presents with breast cancer and is suffering from symptoms including damaged breast tissue and breast pain. She is administered a tablet containing glucoraphanin, myrosinase, ascorbic acid, and a shiitake mushroom extract. The tablet is an enteric coated formulation which releases the contents in the small intestine. After one month of daily administration of the tablet, the subject experiences modulation of surrogate biomarkers including NQO1 which correlate with improvement in symptoms.

Example 11

The following study was conducted to determine the effect of the combination of sulforaphane and *Moringa* plant components on the gene expression of Nrf2-regulated NAD (P)H:quinone dehydrogenase 1 (NQO1). An Nrf2 pathway plays a role in combating oxidative stress in articular cartilage. During the development of osteoarthritis, excessive reactive oxygen species (ROS) are produced and function as a secondary messenger that reduces extracellular matrix (ECM) synthesis and induces chondrocyte apoptosis. Therefore, the induction of NQO1 gene expression would be beneficial in neutralizing ROS and provide defense against the breakdown of ECM and chondrocyte cell death.

Figure 5A:
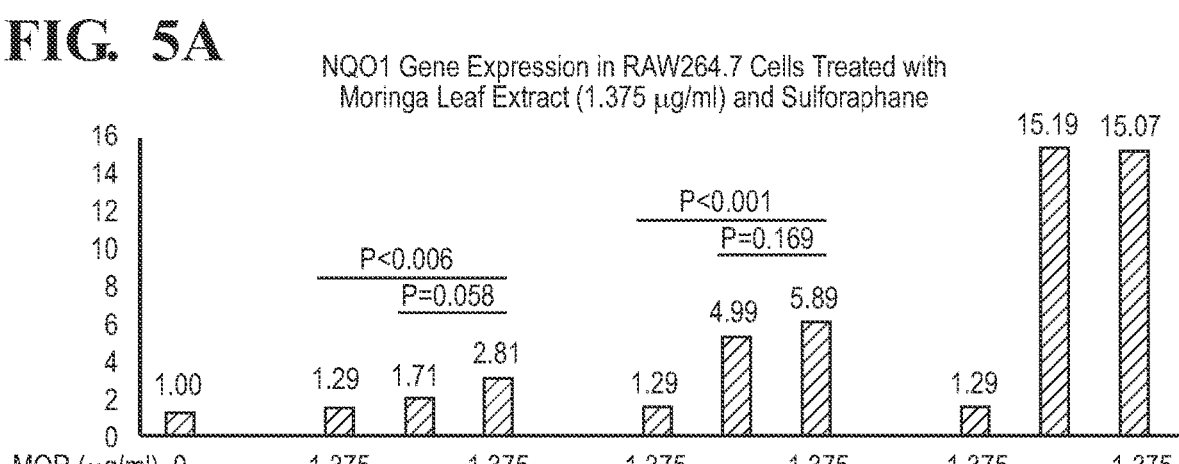
FIGS. 5A-5C are graphs showing the results of the experiment described in Example 11.
Figure 5B:
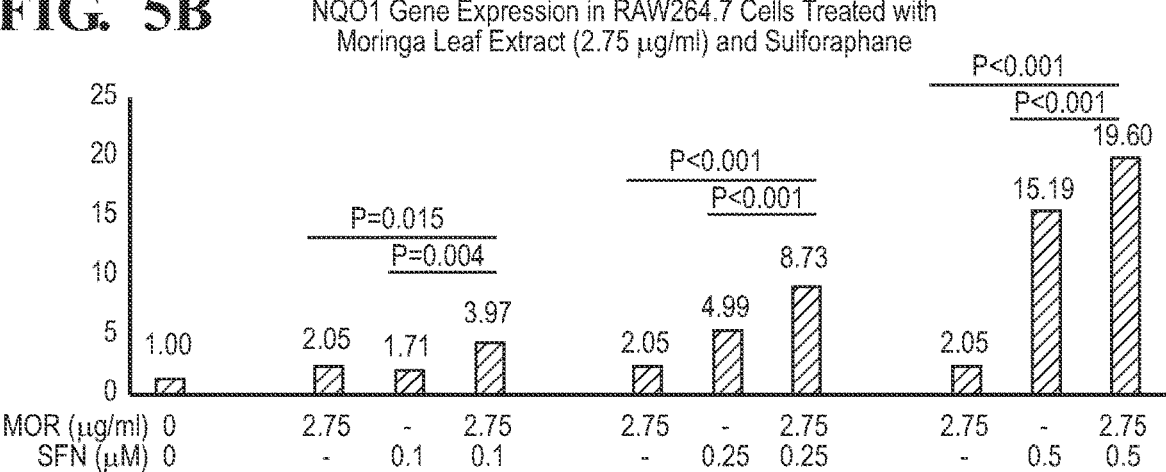
Figure 5C:
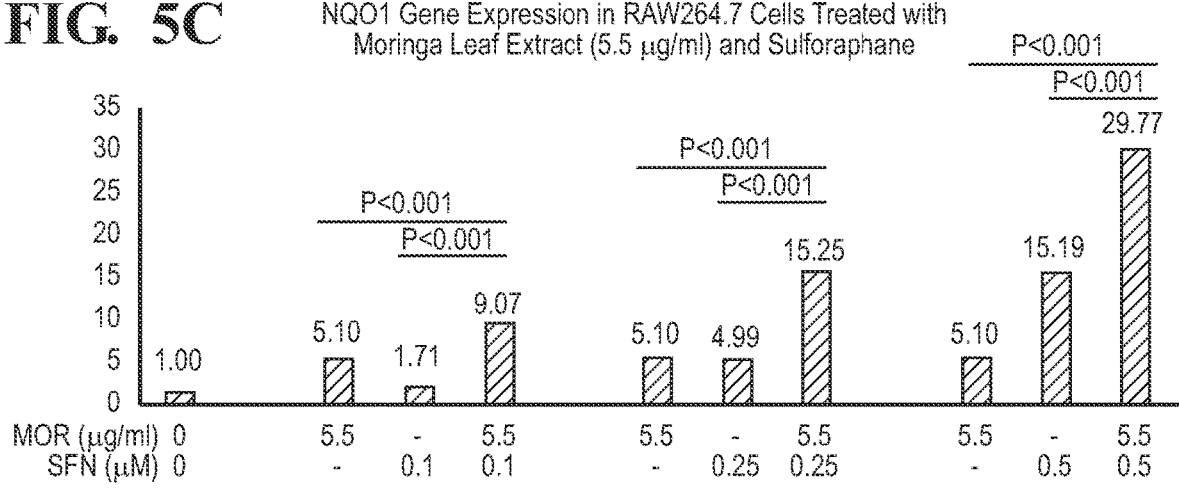

In the study, the macrophage cell line RAW 264.7 was treated with sulforaphane (SFN), *Moringa* plant components (MOR), or a combination of SFN and MOR, for 24 hours. In particular, the cells were treated with one of the following: (i) 0 μg/mL MOR and 0 μM SFN (control), (ii) 1.375 μg/mL MOR, (iii) 0.1 μM SFN, (iv) 0.25 μM SFN, (v) 0.5 μM SFN, (vi) 1.375 μg/mL MOR and 0.1 μM SFN, (vii) 1.375 μg/mL MOR and 0.25 μM SFN, (viii) 1.375 μg/mL MOR and 0.5 μM SFN, (ix) 2.75 μg/mL MOR, (x) 2.75 μg/mL MOR and 0.1 μM SFN, (xi) 2.75 μg/mL MOR and 0.25 μM SFN, (xii) 2.75 μg/mL MOR and 0.5 μM SFN, (xiii) 5.5 μg/mL MOR, (xiv) 5.5 μg/mL MOR and 0.1 μM SFN, (xv) 5.5 μg/mL MOR and 0.25 μM SFN, and (xvi) 5.5 μg/mL MOR and 0.5 μM SFN. The gene expression of NQO1 was analyzed via quantitative RT-PCR. The results, which are depicted in FIGS. 5A-5C, show the following:

The results demonstrate that compared to each component alone, the combination of sulforaphane and *Moringa* plant components had a synergistic effect on the gene expression of NQO1. Particularly, the synergistic effect was statistically significant when the cells were treated with a combination of 2.75 μg/mL MOR and any of the three concentrations of SFN (i.e., 0.1 μM SFN, 0.25 μM SFN, and 0.5 μM SFN). Further, the synergistic effect was statistically significant when the cells were treated with a combination of 5.5 μg/mL MOR and any of the three concentrations of SFN (i.e., 0.1 μM SFN, 0.25 μM SFN, and 0.5 μM SFN).

The foregoing descriptions of various embodiments of the invention are provided for purposes of illustration, and are not intended to be exhaustive or limiting. Modifications or variations are also possible in light of the above teachings. The composition may include other components, such as vitamins (especially vitamin E), selenium, probiotics, D-Mannose, and others. Also, it may include glucoraphanin without myrosinase, myrosinase without glucoraphanin, or any combination or the two. The embodiments described above were chosen to provide the best application to thereby enable one of ordinary skill in the art to utilize the disclosed inventions in various embodiments and with various modifications as are suited to the particular use contemplated. All such modifications and variations are within the scope of the invention as set forth in the present disclosure and the appended drawing FIGS. 1-5, which are incorporated by reference herein in their entirety.

What is claimed is:

1. A composition comprising:

a *Moringa* plant component in an amount of 1 milligram (mg) to 1750 mg; and a sulforaphane derivative in an amount of 1 mg to 50 mg, wherein the sulforaphane derivative includes at least one of sulfoxythiocarbamate analogues of sulforaphane and 6-methylsulfinylhexyl isothiocyanate (6-HITC);

wherein the *Moringa* plant component and the sulforaphane derivative are present in amounts synergistically effective to increase gene expression of heme oxygenase-1 (HMOX1) or gene expression of Nrf2-regulated NAD(P)H:quinone dehydrogenase 1 (NQO1) in a subject.

2. A composition according to claim 1 including the *Moringa* plant component in an amount of 100 mg to 100 mg; and the sulforaphane derivative in an amount of 1 mg to 15 mg.

3. A composition according to claim 1, wherein the *Moringa* plant component is *Moringa* leaf extract containing 10 mg of moringin per 1000 mg of the *Moringa* leaf extract.

4. A composition according to claim 1 further comprising a mushroom extract or powder.

5. A composition according to claim 1 further comprising a broccoli extract or powder.

6. A composition comprising:

a *Moringa* plant component an amount of 150 to 1500 mg; and a sulforaphane precursor in an amount of 1 to 100 mg, wherein the sulforaphane precursor is glucoraphanin;

wherein the *Moringa* plant component and the sulforaphane precursor are present in amounts synergistically effective to increase gene expression of heme oxygenase-1 (HMOX1) or gene expression of Nrf2-regulated NAD(P)H:quinone dehydrogenase 1 (NQO1) in a subject.

7. A composition according to claim 6, wherein the *Moringa* plant component is *Moringa* leaf extract containing 10 mg of moringin per 1000 mg of the *Moringa* leaf extract.

8. A composition according to claim 6, wherein the *Moringa* plant component includes a glucosidase enzyme capable of converting the sulforaphane precursor to sulforaphane.

9. A composition according to claim 8, wherein the glucosidase enzyme is a thioglucosidase enzyme.

10. A composition according to claim 9, wherein the thioglucosidase enzyme is myrosmase.

11. A composition according to claim 6 further comprising a mushroom extract or powder.

12. A composition according to claim 6 further comprising a broccoli extract or powder.

* * * * *